(12) United States Patent
Raad et al.

(10) Patent No.: US 9,913,820 B2
(45) Date of Patent: *Mar. 13, 2018

(54) ANTIMICROBIAL COMPOSITIONS COMPRISING GLYCERYL NITRATES

(71) Applicant: Board of Regents, The University of Texas System, Austin, TX (US)

(72) Inventors: Issam Raad, Missouri City, TX (US); Joel Rosenblatt, Pottstown, PA (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/260,238

(22) Filed: Sep. 8, 2016

(65) Prior Publication Data
US 2016/0374978 A1    Dec. 29, 2016

Related U.S. Application Data

(63) Continuation of application No. 14/420,179, filed as application No. PCT/US2013/054129 on Aug. 8, 2013, now Pat. No. 9,457,002.

(Continued)

(51) Int. Cl.

| | | |
|---|---|---|
| *A61K 31/21* | (2006.01) |
| *A61K 33/40* | (2006.01) |
| *A61K 31/194* | (2006.01) |
| *A61K 31/19* | (2006.01) |
| *A61K 9/00* | (2006.01) |
| *A61K 31/095* | (2006.01) |
| *A61K 31/10* | (2006.01) |
| *A61K 9/08* | (2006.01) |
| *A61L 29/16* | (2006.01) |
| *A61K 31/045* | (2006.01) |
| *A61K 31/16* | (2006.01) |
| *A61K 31/145* | (2006.01) |
| *A61K 31/185* | (2006.01) |
| *A61K 31/191* | (2006.01) |
| *A61K 31/198* | (2006.01) |
| *A61K 31/20* | (2006.01) |
| *A61K 31/327* | (2006.01) |
| *A61K 31/7004* | (2006.01) |
| *A61K 33/42* | (2006.01) |
| *A61L 31/16* | (2006.01) |
| *A61L 15/46* | (2006.01) |
| *A61L 17/00* | (2006.01) |
| *A61K 45/06* | (2006.01) |
| *A01N 31/02* | (2006.01) |
| *A01N 33/20* | (2006.01) |
| *A01N 37/16* | (2006.01) |
| *A01N 37/36* | (2006.01) |
| *A01N 37/44* | (2006.01) |
| *A01N 59/00* | (2006.01) |
| *C11D 3/20* | (2006.01) |

(Continued)

(52) U.S. Cl.
CPC ............. *A61K 31/21* (2013.01); *A01N 25/02* (2013.01); *A01N 31/02* (2013.01); *A01N 33/16* (2013.01); *A01N 33/20* (2013.01); *A01N 37/16* (2013.01); *A01N 37/36* (2013.01); *A01N 37/44* (2013.01); *A01N 59/00* (2013.01); *A61K 9/0014* (2013.01); *A61K 9/08* (2013.01); *A61K 31/045* (2013.01); *A61K 31/095* (2013.01); *A61K 31/10* (2013.01); *A61K 31/145* (2013.01); *A61K 31/16* (2013.01); *A61K 31/185* (2013.01); *A61K 31/19* (2013.01); *A61K 31/191* (2013.01); *A61K 31/194* (2013.01); *A61K 31/198* (2013.01); *A61K 31/20* (2013.01); *A61K 31/327* (2013.01); *A61K 31/7004* (2013.01); *A61K 33/40* (2013.01); *A61K 33/42* (2013.01); *A61K 45/06* (2013.01); *A61K 47/10* (2013.01); *A61K 47/12* (2013.01); *A61K 47/20* (2013.01); *A61K 47/24* (2013.01); *A61L 15/46* (2013.01); *A61L 17/005* (2013.01); *A61L 29/16* (2013.01); *A61L 31/16* (2013.01); *C11D 3/2003* (2013.01); *C11D 3/2065* (2013.01); *C11D 3/2075* (2013.01); *C11D 3/3947* (2013.01); *C11D 7/261* (2013.01); *C11D 7/265* (2013.01); *C11D 11/0041* (2013.01); *A61L 2202/21* (2013.01); *A61L 2300/216* (2013.01); *A61L 2300/404* (2013.01)

(58) Field of Classification Search
None
See application file for complete search history.

(56) References Cited

U.S. PATENT DOCUMENTS

| | | |
|---|---|---|
| 4,919,919 A | 4/1990 | Aouda et al. |
| 5,217,493 A | 6/1993 | Raad et al. |

(Continued)

FOREIGN PATENT DOCUMENTS

EP    0039999    11/1981

OTHER PUBLICATIONS

Bátai et al., "The growth of bacteria in intravenous glyceryl trinitrate and in sodium nitroprusside," *Anesth. Analg.*, 89:1570-1572, 1999.

(Continued)

*Primary Examiner* — Kristin Vajda
(74) *Attorney, Agent, or Firm* — Parker Highlander PLLC

(57) ABSTRACT

Provided are antimicrobial solutions comprising a glyceryl nitrate (e.g., glyeryl trinitrate) in combination with a chelator (e.g., citrate), a peroxide, a fatty acid, and/or an alcohol (e.g., ethanol). In various aspects these components may synergistically act to kill or reduce the growth of microbes, such as bacteria or fungi, present in a biofilm.

43 Claims, 17 Drawing Sheets

Related U.S. Application Data

(60) Provisional application No. 61/680,964, filed on Aug. 8, 2012.

(51) Int. Cl.

| | | |
|---|---|---|
| *C11D 3/39* | (2006.01) | |
| *C11D 7/26* | (2006.01) | |
| *C11D 11/00* | (2006.01) | |
| *A01N 25/02* | (2006.01) | |
| *A01N 33/16* | (2006.01) | |
| *A61K 47/10* | (2017.01) | |
| *A61K 47/12* | (2006.01) | |
| *A61K 47/20* | (2006.01) | |
| *A61K 47/24* | (2006.01) | |

(56) References Cited

U.S. PATENT DOCUMENTS

| | | | |
|---|---|---|---|
| 5,624,704 | A | 4/1997 | Darouiche et al. |
| 5,814,666 | A | 9/1998 | Green et al. |
| 5,902,283 | A | 5/1999 | Darouiche et al. |
| 6,267,979 | B1 | 7/2001 | Raad et al. |
| 7,651,661 | B2 | 1/2010 | Raad et al. |
| 9,457,002 | B2 * | 10/2016 | Raad .................. A61K 45/06 |
| 2002/0049188 | A1 | 4/2002 | Azarnoff et al. |
| 2003/0078242 | A1 | 4/2003 | Raad et al. |
| 2005/0197634 | A1 | 9/2005 | Raad et al. |
| 2007/0154621 | A1 | 7/2007 | Raad |
| 2008/0183152 | A1 | 7/2008 | Raad et al. |
| 2009/0312279 | A1 | 12/2009 | Mookerjee et al. |
| 2010/0055086 | A1 | 3/2010 | Raad |
| 2011/0201692 | A1 | 8/2011 | Raad |
| 2011/0311602 | A1 | 12/2011 | Mills et al. |
| 2012/0064372 | A1 | 3/2012 | Raad |

OTHER PUBLICATIONS

Crnich et al., "Prospective Randomized Double-Blind Trial of an Ethanol Lock for Prevention of CLABSI," Abstract, In: 49th Interscience Conference on Antimicrobial Agents and Chemotherapy. San Francisco, USA. 2009.

Extended European Search Report issued in European Application No. 13827577.1, dated Dec. 7, 2015.

Fang, "Mechanisms of nitric oxide-related antimicrobial activity," *Journal of Clinical Investigation*, 99(12):2818-2825, 1997.

Marshall and White, "Complete denitration of nitroglycerin by bacteria isolated from a washwater soakaway," *Applied and Environmental Microbiology*, 67(6):2622-2626, 2001.

Muri et al., "Hydroxamic acids as pharmacological agents," *Curr Med Chem.*, 9(17):1631-1653, 2002.

Office Action issued in Australian Application No. 2013299575, dated Nov. 24, 2016.

Office Action issued in U.S. Appl. No. 14/420,179, dated Oct. 15, 2015.

Pal and Saha, "Hydroxamic acid—A novel molecule for anticancer therapy," *J Adv Pharm Technol Res.*, 3(2): 92-99, 2012.

Palmeira-de-Oliveira et al., "In Vitro anti-*candida* activity of lidocaine and nitroglycerin: alone and combined," *Infectious Diseases in Obstetrics and Gynecology*, 2012:727248, 2012.

PCT International Search Report and Written Opinion issued in International Application No. PCT/US2013/054129, dated Oct. 15, 2013.

Rosenblatt et al., "Captylic acid and glyceryl trinitrate combination for eradication of biofilm," *Antimicrobial Agents and Chemotherapy*, 59(3):1786-1788, 2015.

Rosenblatt et al., "Glyceryl trinitrate complements citrate and ethanol in a novel antimicrobial catheter lock solution to eradicate biofilm organisms," *Antimicrobial Agents and Chemotherapy*, 57(8):3555-3560, 2013.

Rosenblatt et al., "Optimized Glyceryl Trinitrate (GTN)-Citrate-Ethanol Non-antibiotic, Antimicrobial Catheter Lock Solution for Prevention of Central Line Associated Bloodstream Infections (CLABSIs)," Presentation L-410, 54th ICAAC (Interscience Conference on Antimicrobial Agents and Chemotherapy), Washington, DC, 2014.

Slobbe et al., "Prevention of Catheter-Related Bacteremia with a Daily Ethanol Lock in Patients with Tunneled Catheters: A Randomized, Placebo-Controlled Trial," *PLoS ONE*, 5(5): e10840, 2010.

Sudhamsu and Crane, "Bacterial nitric oxide synthases: what are they good for?" *Trends in Microbiology*, 17(5):212-218, Abstract Only, 2009.

Weijmer et al., "Superior antimicrobial activity of trisodium citrate over heparin for catheter locking," *Nephrol Dial Transplant*, 17:2189-2195, 2002.

* cited by examiner

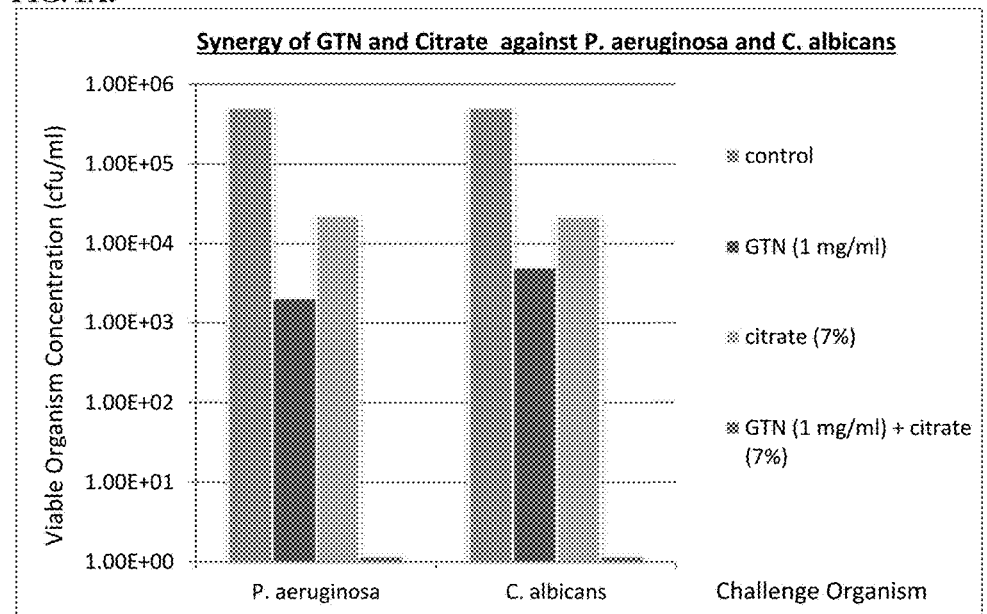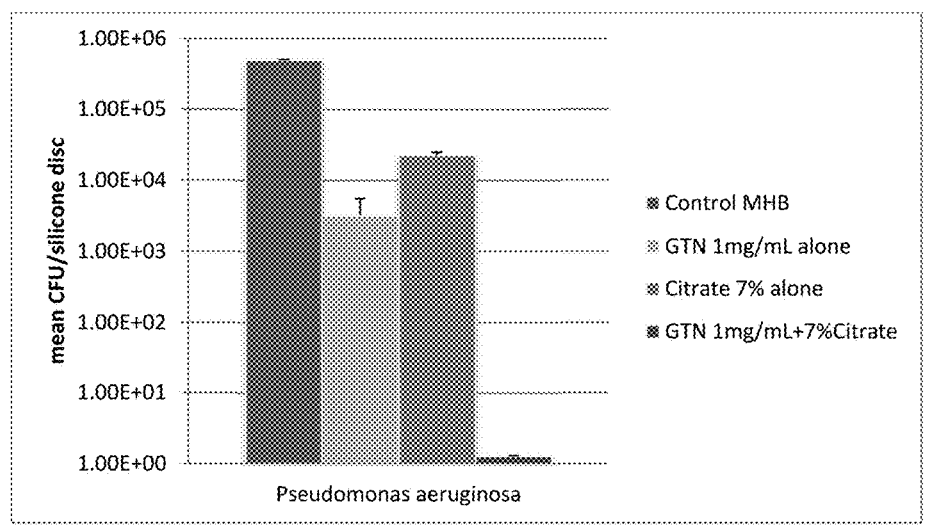
FIGS. 1A-B

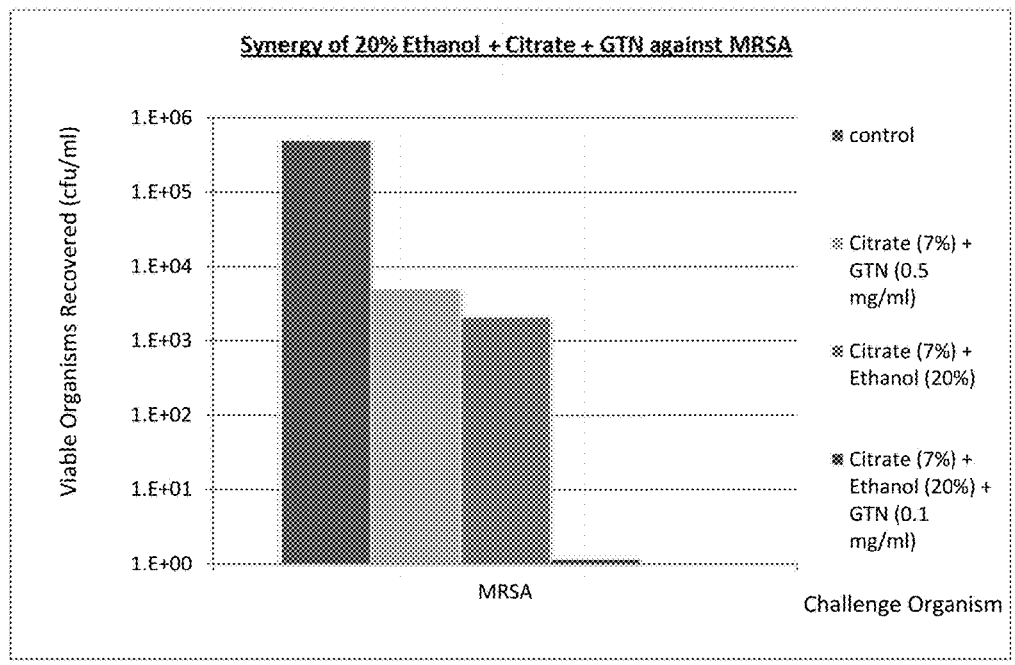
Synergy of 20% Ethanol, Citrate and GTN
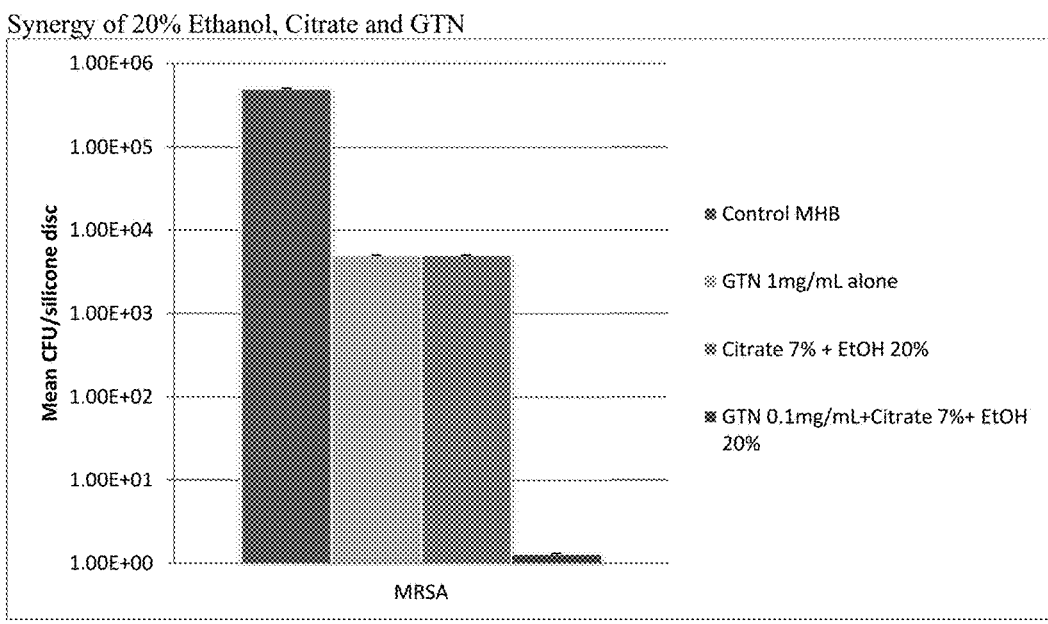
FIG. 7

ANTIMICROBIAL COMPOSITIONS COMPRISING GLYCERYL NITRATES

This application is a continuation of U.S. application Ser. No. 14/420,179, filed Feb. 6, 2015, which is a national phase application under 35 U.S.C. § 371 of International Application No. PCT/US2013/054129, filed Aug. 8, 2013, which claims the benefit of U.S. Provisional Patent Application No. 61/680,964, filed Aug. 8, 2012, the entirety of each of which is incorporated herein by reference.

BACKGROUND OF THE INVENTION

1. Field of the Invention

The present invention relates generally to the field of molecular biology and medicine. More particularly, it concerns antimicrobial compositions comprising a glyceryl nitrate.

2. Description of Related Art

Currently, compositions for biofilm eradication where contact with humans or animals can occur generally require high alcohol concentrations, antibiotics and/or relatively toxic concentrations of antiseptic agents. Antibiotics are often expensive and their prophylactic use is problematic due to the potential for inducing antimicrobial resistance.

Vascular catheters are currently hydraulically locked with saline or heparin solutions between infusions or blood sampling through lumens. The hydraulically locked lumens are generally capped off between uses. Lumens can become contaminated with bacteria or fungi through introduction of contaminated infusates, by environmental exposure when uncapped, or through manual contact with luers and/or caps. In the case of suspected bloodstream infections for catheterized patients, disinfection and salvage of the catheter with an antimicrobial lock can be employed. Antibiotic lock solutions are frequently used but have the disadvantages of being expensive and risking the development of antibiotic-resistant organisms. Infections from antibiotic resistant organisms typically have higher treatment costs and mortalities. High concentration ethanol solutions have also been attempted. Flushing of a 70% ethanol lock solution did not produce a significant reduction in infection and was associated with a higher indigence of non-severe complaints associated with inebriation (Slobbe et al., Prevention of Catheter-Related Bacteremia with a Daily Ethanol Lock in Patients with Tunneled Catheters: A Randomized, Placebo-Controlled Trial, PLoS ONE 5(5): e10840). A prophylactic clinical trial involving 1-3 hours of locking with 50% ethanol was not effective in reducing infection in hospitalized patients with long-term catheters (Crnich et al., Prospective Randomized Double-Blind Trial of an Ethanol Lock for Prevention of CLABSI [Abstract]. In: 49th Interscience Conference on Antimicrobial Agents and Chemotherapy. San Francisco, USA. 2009).

Microorganisms present in biofilms can be particularly difficult to eradicate. Biofilm phenotypes are important in recalcitrant device-associated and nosocomial infections and are much more difficult to eradicate than microbes in the dilute planktonic state. Biofilm formation is often an important part of generating an infection by a bacterial or fungal organism. In addition, biofilm formation can cause odor, discoloration, degradation and other significant problems by fouling pipes and other industrial equipment. One medical application of particular interest is disinfection of the lumenal surfaces of vascular catheters. Intralumenal infections are a significant problem for long term catheterized patients who require vascular access for infusion of medications or nutrition. In between catheter uses, the lumens of the catheters are typically locked with saline or heparin-saline solutions to prevent blood from clotting and occluding the lumens. Through the course of handling during access procedures or through use of contaminated infusates catheter lumens can become colonized by pathogenic organisms and can become a source of bacteremias or candidemias. Lumenal sourced colonization is the most common cause of late-onset catheter-associated blood stream infections. Clearly, there is a need for new antimicrobial compositions that may be used to kill microorganisms present in biofilms.

SUMMARY OF THE INVENTION

The present invention overcomes limitations in the prior art by providing new antimicrobial compositions and methods. In certain aspects, an antimicrobial solution comprising a glyceryl nitrate such as, e.g., glyceryl trinitrate (GTN, nitroglycerin), in combination with a chelator, a peroxide, a fatty acid, and/or an alcohol are provided and may be used, e.g., to effectively kill microorganisms in biofilms. The present invention is based, in part, on the discovery that GTN in combination with a chelator and/or an alcohol may be used to synergistically kill microorganisms present in biofilms such as bacteria or fungi. In certain aspects, solutions of the present invention may be used as antimicrobial solutions on medical equipment (e.g., used as a locking solution in a catheter), for cleaning or flushing oil or gas pipelines, on a food preparation surface, for wound treatment, on periodontal or dental devices or during an oral surgery or dental procedure, or in skin cleaning or antisepsis. An aspect of the present invention relates to an antimicrobial solution comprising a glyceryl nitrate and: an alcohol at a level of greater than about 10% (v/v), a peroxide, a fatty acid, and/or a chelator. The solution may be a liquid, a suspension, or an emulsion in a fluid medium. The solution may comprise the glyceryl nitrate and the chelator. The solution may comprise the glyceryl nitrate, the peroxide, and the chelator. The peroxide may be at a level of about 0.01-10%, more preferably about 0.1-3%, even more preferably about 0.1-2%. In some embodiments, the solution comprises the glyceryl nitrate, the fatty acid, and the chelator. The fatty acid may be at a level of about 0.001-10%, more preferably about 0.01-5%, more preferably about 0.05-3%. In some embodiments, the solution comprises the glyceryl nitrate and the peroxide. The peroxide may be hydrogen peroxide, benzoyl peroxide, or barium peroxide. In some embodiments, the peroxide is an inorganic peroxide such as barium peroxide, calcium peroxide, magnesium peroxide, or strontium peroxide. In some embodiments, the peroxide is hydrogen peroxide. The solution may comprise about 0.1-3% hydrogen peroxide. The solution may further comprise the chelator. In some embodiments, the solution comprises GTN, the fatty acid, and the chelator. The fatty acid may be a $C_{6-12}$ alkanoic acid or a $C_{6-10}$ alkanoic acid. In some embodiments, the fatty acid is hexanoic acid, octanoic acid, decanoic acid, dodecanoic acid, caprylic acid (octanoic acid), caproic acid, or lauric acid. In some embodiments, the fatty acid is caprylic acid (octanoic acid). The solution may comprise about 0.01-5% caprylic acid. The solution may further comprise a surfactant, wetting agent, emollient, moisturizer, scent, or a flavor agent. In some embodiments, one or more polymer(s) may be added to the antimicrobial solution to thicken the solution or make the solution more viscous. Antimicrobial solutions containing the polymers as thickeners or to increase the viscosity may be useful, e.g., in or as a coating. For example, the coating may be comprised on or applied to a medical device, or the may coating be applied to a subject topically or parenterally, e.g., to reduce the growth of or kill bacteria and fungi.

The solution may comprise the glyceryl nitrate and the alcohol. In some embodiments, the solution comprises the glyceryl nitrate, the alcohol, and the chelator. The glyceryl nitrate may be glyceryl trinitrate (GTN). The glyceryl trinitrate may have a concentration of from about 0.05 to about 1500 micrograms/ml, from about 1 to about 1000 micrograms/ml, or from about 10 to about 500 micrograms/ml. The glyceryl nitrate may be glyceryl dinitrate or glyceryl mononitrate. The chelator may be citrate, a tetra acetic acid, a thiosulfate, N-acetyl cysteine, disulfiram, a hydroxy acid, a hydroxamic acid, ethylene diaminedisuccinate (EDDS), Tetrakis hydroxymethyl phosphonium sulfate (THPF), or MesNA. The chelator may be citrate. The chelator may be ethylene diaminedisuccinate (EDDS) or Tetrakis hydroxymethyl phosphonium sulfate (THPF). In some embodiments, the chelator is a hydroxy acid, such as an α-hydroxy acid. The hydroxy acid may be lactic acid, gluconic acid, glycolic acid, galacturonic acid, salicylic acid, or glucaronic acid. In some embodiments, the chelator is a hydroxamic acid. The hydroxamic acid may be hydroxamic acid, benzohydroxamic acid, salicylhydroxamic acid, or suberoylanilide hydroxamic acid (SAHA). The citrate may comprise about 0.1-10%, about 1-10%, about 3.5-7%, or about 4% (v/v) of the solution. The chelator may be MesNA. The MesNA may comprise about 1-10%, or about 5% (v/v) of the solution. The chelator may be disulfiram. The disulfiram may have a concentration of about 0.05-5 mg/ml or about 0.1-0.5 mg/ml. The alcohol may be ethanol, methanol, isopropanol, butyl alcohol, propylene glycol, benzyl alcohol, chlorobutanol or phenylethyl alcohol. The alcohol may comprise from greater than about 10% to about 80% (v/v), from greater than 10 to about 40%, from about 15-30%, or about 20% of the solution. The solution may be further defined as a pharmaceutically acceptable composition or a pharmaceutically acceptable excipient. In some embodiments, the solution comprises from greater than 10% to about about 60% ethanol, about 1-20% citrate, and about 10-500 microgram/nil glyceryl trinitrate. In some embodiments, the solution comprises from about 15% to about 30% ethanol, about 2.5-10% citrate, and about 50-250 microgram/nil glyceryl trinitrate.

Another aspect of the present invention relates to a method for reducing microbial organisms from a surface comprising contacting the surface with an antimicrobial solution of the present invention for an amount of time sufficient to reduce microbial organisms on the surface. The microbial organisms may be present in a biofilm on the surface. The surface may be comprised on a catheter, a medical device, a water pipeline, a fluid pipeline, an oil or gas pipeline, an ice machine pipe, or a beverage dispensing pipe. In some embodiments, the surface is comprised on the interior of a vascular catheter.

In some embodiments, the antimicrobial solution is used as a locking solution or a flush solution for a medical device such as, e.g., a catheter, or the antimicrobial solution may be applied to a subject topically (e.g., to disinfect a portion of the skin of a subject or to clean or disinfect a wound on a subject). For example, a solution comprising a glyceryl nitrate (e.g., GTN), a fatty acid (e.g., $C_{6-12}$ alkanoic acid, a $C_{6-10}$ alkanoic acid, capyrilic acid), and a chelator may be used as a flush solution. The flush solution may, e.g., be used to flush a catheter or other medical device. In some embodiments, the flush solution may be applied to, used to irrigate or clean, or used at a lavage for a wound on s subject, such as a human subject. These approaches may be particularly useful in subjects who have a wound that may comprise bacteria that are resistant to antibiotics or other treatment, or where the subject is immunosuppressed, e.g., as a result of an infection or disease such as cancer, HIV infection, etc. In some embodiments, a solution comprising a glyceryl nitrate (e.g., GTN), an alcohol (e.g., ethanol), and a chelator may be used as a locking solution. As shown in the below examples, a solution comprising GTN, 20% ethanol, and chelator was shown to exhibit a 1 year shelf stability.

Yet another aspect of the present invention relates to a kit comprising an antimicrobial solution of the present invention in a suitable container means. The kit may further comprise instructions for use. The suitable container means may be a vial, syringe or dispenser. The solution may be comprised in or on a swab or wipe.

Another aspect of the present invention relates to a method of treating a wound in a subject comprising contacting or administering an antimicrobial solution of the present invention to at least a portion of the wound. Preferably, a therapeutically effective amount of the antimicrobial solution is applied to the wound. The subject may be a human. The solution may be topically administered to the subject. In some embodiments, the solution is administered as a lavage. The method may further comprise irrigating the wound with the solution. The solution may be applied to a wound bed, an epithelial tissue, an endothelial tissue, or an organ surface.

In some embodiments, the kit comprises an antimicrobial solution in a container that is designed to allow for the solution to be dispensed as a locking solution. For example, the solution may be comprised in a vial or syringe and added or dispensed onto or into a medical device such as, e.g., a catheter. The kit may contain instructions for use during a medical or cleaning procedure. The kit may be packaged with one or more syringes, swabs or wipes for application. The solution may be comprised in a syringe, vial, tube, cream, ointment, wipe or film. In some embodiments, the kit comprises a single solution comprising a glyceryl nitrate and a) an alcohol and/or a chelator. In other embodiments the glyceryl nitrate, alcohol, peroxide, fatty acid, and/or chelator may be contained in separate containers in a kit and mixed (e.g., mixed, sonicated, etc.) prior to use. For example, several possibilities are shown below.

| First container means | Second container means | Third container means |
|---|---|---|
| (glyeryl nitrate + alcohol) | chelator | n/a |
| (glyceryl nitrate + chelator) | alcohol or peroxide or fatty acid | n/a |
| glyceryl nitrate | (chelator + alcohol) | n/a |
| glyceryl nitrate | alcohol or peroxide or fatty acid | chelator |
| glyceryl nitrate | (chelator + peroxide) | n/a |
| glyceryl nitrate | (chelator + fatty acid) | n/a |

The duration of contact needed for disinfecting surfaces by fluid contact can vary by organism and/or by how well established a biofilm is being treated. As shown in the below examples, the inventors have found that biofilms can be eradicated within 2 hours by contact with compositions of low enough toxicity that they are suitable for use in intravascular devices.

Other physiologic surfaces which could be treated with the compositions disclosed here include, e.g., skin and wound beds, teeth, the oro and nasopharynx, surgical sites, organs, nerve tissue, tendons, cartilage and bone. In some embodiments, a solution of the present invention may be sprayed, nebulized, or inhaled by a subject into a lung, sinus, or respiratory tissue to treat or clean a wound or tissue, or reduce the growth of bacteria or fungi on the tissue. In some embodiments, a solution of the present invention may be administered topically to a subject, such as a human patient, to treat or prevent a sexually transmitted disease (STD). For contact with physiologic surfaces an antimicrobial composition of the present invention may be formulated into a gel, cream, or film, and the composition may include one or more coloring, aromatic, lubricious, moisturizing, pain relief and/or anti-inflammatory additive. Implanted medical device surfaces to which these compositions can be applied include, but are not limited to, catheters, cords, tubes, drains, shunts, stents, sutures, clips, staples, dressings, meshes, casings, etc. Environmentally exposed surfaces of plants, devices, buildings or machines can be treated with these compositions including surfaces in showers, locker-rooms, bathrooms and medical facilities. Surfaces of personal care and/or protection articles such as gloves, masks, respirators, patches, foot covers, shoe liners, flip flops, ear plugs, nose plugs etc. may be substantially disinfected with these compositions.

The antimicrobial compositions of the present invention may be contacted with a surface for a variety of periods of time to kill microorganisms or reduce the growth of microorganisms. For example, the contacting may be performed for at least 1, 2, 3, 4, 5 hours or at least 1, 2, 3, 4, 5 or more days, or 1, 2, 3, 4, 5 or more weeks, etc. In some embodiments, the contacting may be performed for less than 5, 4, 3, 2, or 1 hours, or less than 45, 30, or 15 minutes.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B: Synergy of GTN and citrate against *P. aeruginosa* and *C. albicans*.

FIG. 7: Synergy of 20% Ethanol, Citrate and GTN.

DESCRIPTION OF ILLUSTRATIVE EMBODIMENTS

Figure 2:
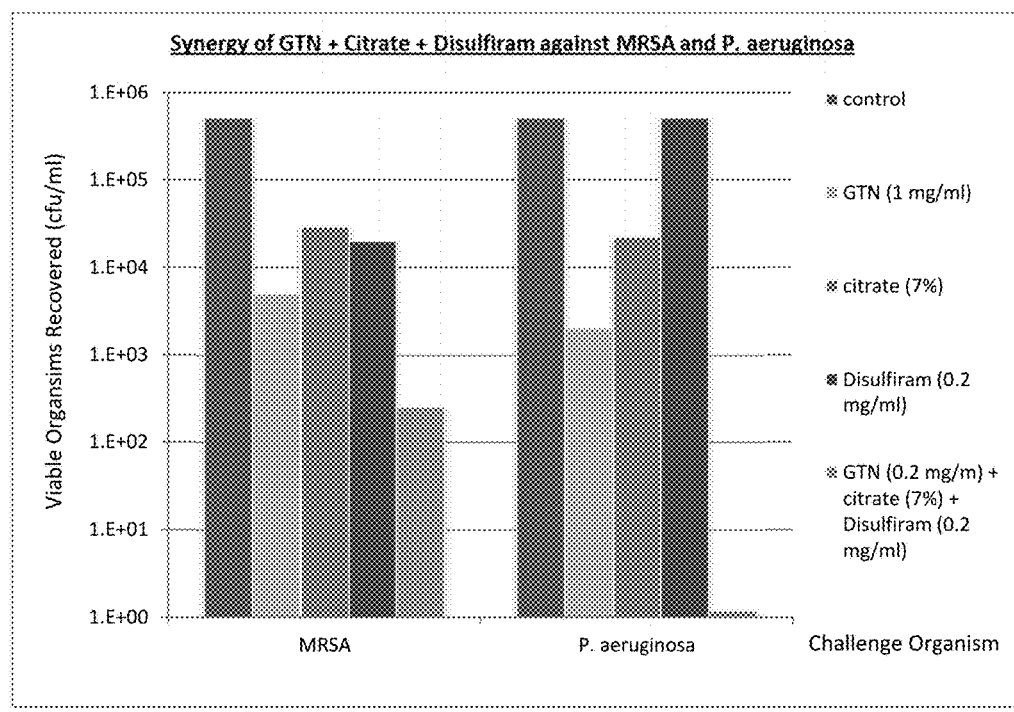
FIG. 2: Synergy of GTN with dual chelators, citrate and disulfiram, at GTN concentration of 0.2 mg/ml against *P. aeruginosa* and MRSA.
Figure 3:
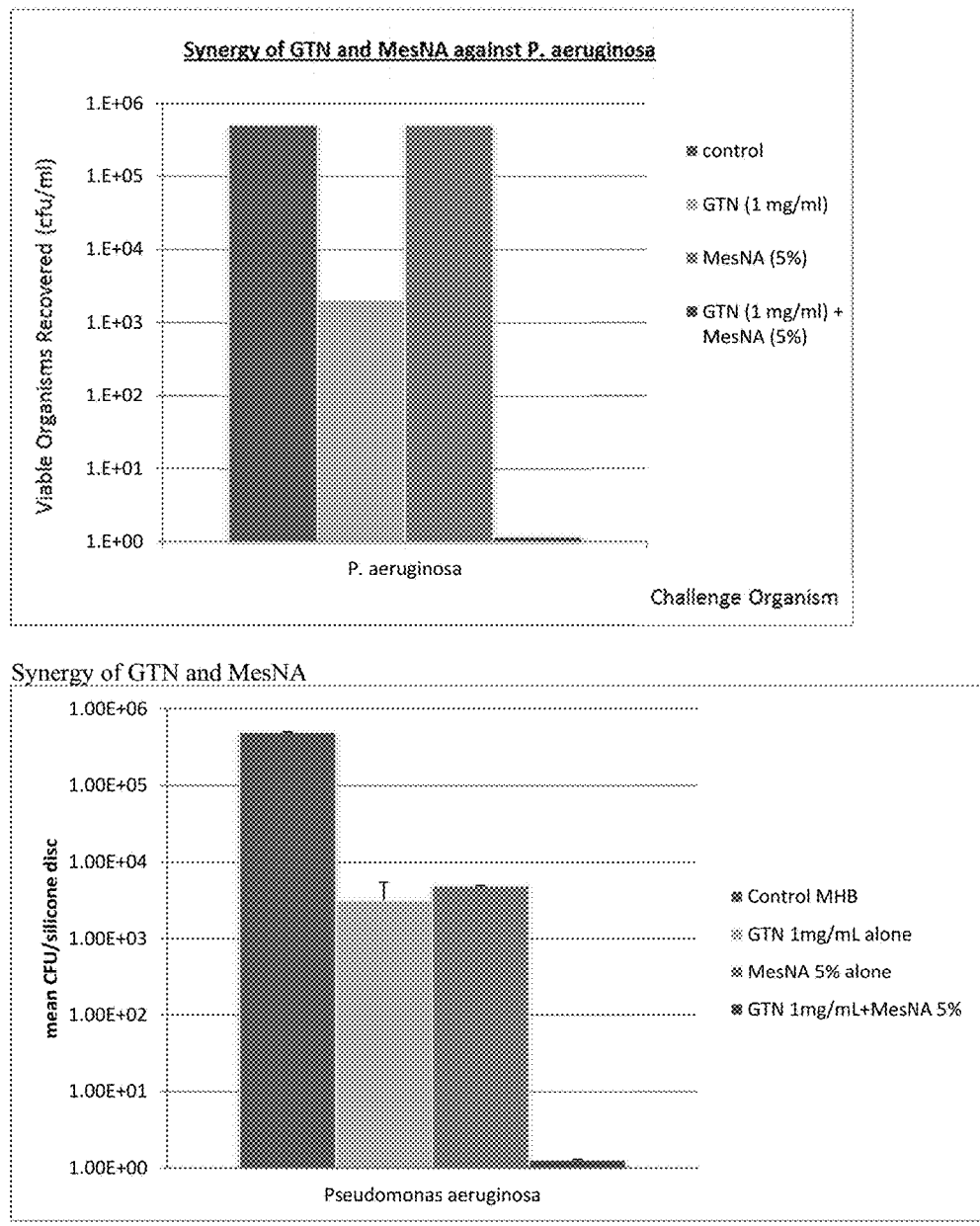
FIG. 3: Synergy of GTN and yet another chelator MesNA against *P. aeruginosa* at a GTN concentration of 1 mg/ml.
Figure 4:
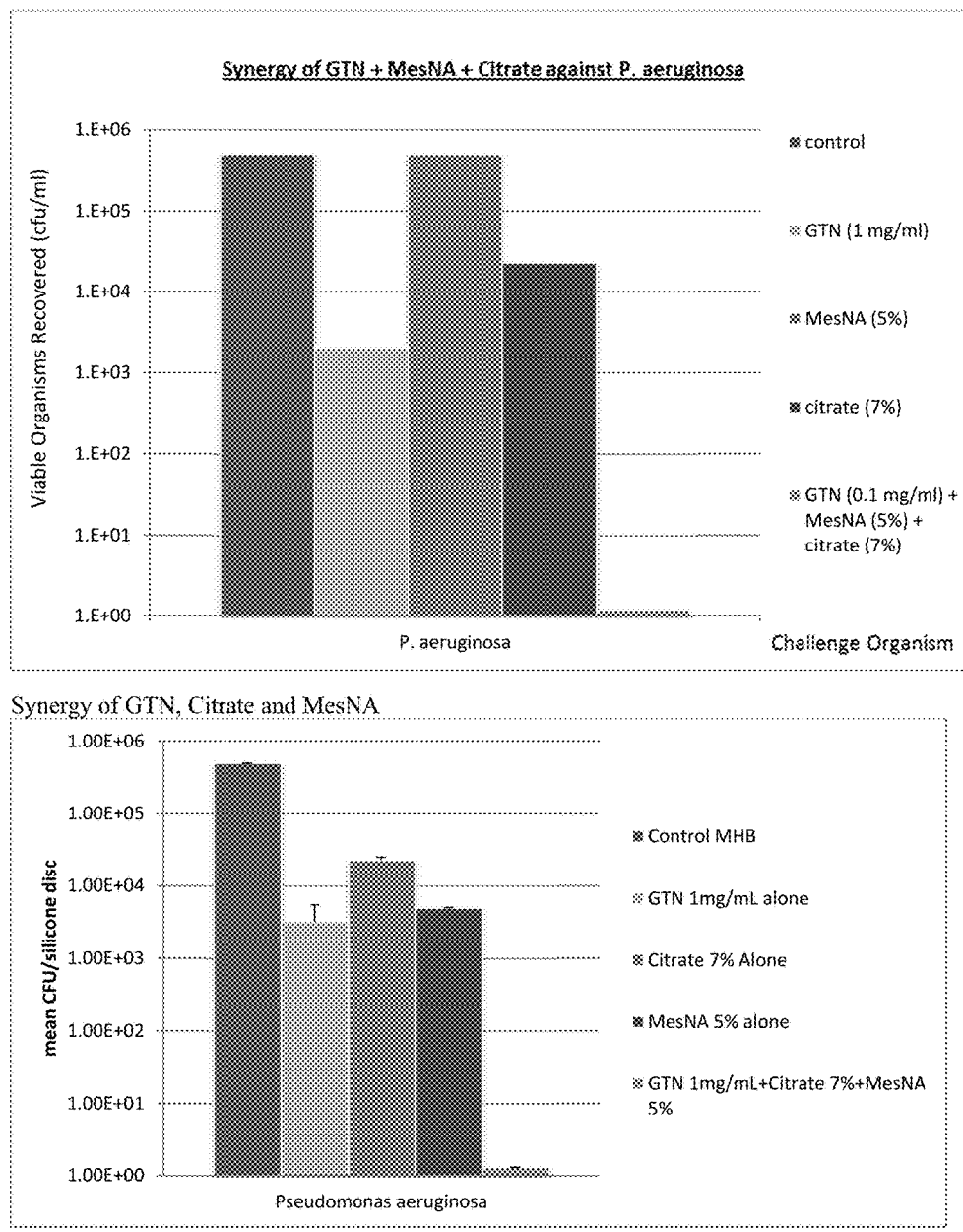
FIG. 4: When citrate and MesNA are used as dual chelators the synergy with GTN against *P. aerugonosa* can be achieved at a GTN concentration of 0.1 mg/ml.

The present invention provides, in various aspects, compositions and methods for inhibiting microbial growth or biofilm formation on surfaces. For example, as shown in the below examples, it has been observed that a glyceryl nitrate can synergize with an alcohol or a chelator to reduce biofilm formation and/or kill microbes present in biofilms. Antimicrobial solutions or compositions provided herein may be used on surfaces in environments and on products used in medical, personal care, food, veterinary, sanitary, industrial and/or communal spaces. In some embodiments, the antimicrobial solutions exhibit little or substantially no mammalian toxicity and/or have little or no adverse impact on materials used to make catheters. In some embodiments, antimicrobial solutions provided herein can be applied topically or to the skin or other tissue of a subject, such as a mammal or human.

Solutions comprising ethanol (e.g., about 10-30%, preferably about 15-20% ethanol) in combination with glyceryl trinitrate (GTN) were observed to synergistically and fully eradicate biofilms within about 2 hours. GTN may be therapeutically attractive for embodiments that involve administration of the agent to a human patient (e.g., in a locking solution) as GTN can be metabolized and cleared rapidly, having a half-life of several minutes. Various GTN concentrations (e.g., about 1-100 micrograms/ml) and lock volumes are well within bolus nitroglycerin intravenous dosage ranges that have been safely used in clinical trials. A variety of citrate concentrations (e.g., about 1-10%, preferably about 7%) may be used and are within concentration ranges that have a history of safe clinical usage. In some embodiments, antimicrobial solutions provided herein may provide a safer and less expensive composition for antimicrobial lock therapy. As shown in the below examples, GTN was observed to demonstrate synergy in bacterial killing or biofilm treatment when combined with peroxide, chelator, (alcohol and chelator), or (fatty acid and chelator). As shown the below examples, biofilm destruction may be achieved with a solution of the present invention in less than or equal to about 15 min for gram negative bacteria and less than or equal to about 30 min for gram positive in dilute concentrations.

The antimicrobial solutions of the present invention may be used, e.g., to disinfect a surface of a medical device, or they may be used to clean the skin or a wound of or on a subject, such as a mammalian subject or a human patient. In some embodiments, the solution may be administered to the subject, e.g., as a flush solution for a catheter, or the solution may be used to clean or irrigate a wound or in a lavage to treat a wound. In some embodiments, the solution may be used topically on the subject, e.g., to clean the skin of the subject prior to insertion of a needle into the subject.

I. Definitions

The terms "antimicrobial medical device" and "medical device" as used herein, refer to an instrument, apparatus, implement, machine, contrivance, implant, or other similar or related article, including a component part, or accessory, which is subjected to sequential antimicrobial contact as described, and is intended for use in the diagnosis, treatment, and/or prevention of disease or other health-related condition in a subject. The subject can be any vertebrate, such as a mammal or a human. Non-limiting examples of antimicrobial medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like; urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, gloves (including latex, non-latex and nitrile), other medical garb, charts, bed rails, condoms, colorectal tract implants, male and female reproductive implants, cosmetic or reconstructive implants (e.g., breast, chin, cheek, buttock, nasal), medical device envelopes and pouches, including stethoscope drums, orthopedic implants (e.g., joint (knee, hip, elbow, shoulder, ankle), prostheses, external fixation pins, intramedullary rods and nails, spine implants), other medical and indwelling devices that may be subject to microbial infestation and/or activity;

and metallic devices, such as cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device. In some embodiments, antimicrobial compositions or solutions of the present invention may be used to substantially disinfect or reduce the growth of a microorganism (e.g., a bacteria of fungi) on a lumenal surface of a vascular catheter; for example the antimicrobial composition or solution may be used to flush the catheter and/or as a locking solution.

The term "antimicrobial agent", as used herein, refers to an agent, such as an antibiotic or an antiseptic, capable of preventing or reducing the growth or reproduction of a microorganism, such as a bacterial or fungal microorganism, or of killing a microorganism.

The term "antibiotic" as used herein refers to a compound or agent that is capable of preventing or reducing the growth or reproduction of a bacterium, or of killing a bacterium or fungal organism. Such agents are generally applied in the treatment of systemic infection in a subject. Non-limiting classes of antibiotics include, e.g., a tetracycline, minocycline, a rifamycin, neomycins, bacitracin, polymixins, aminoglycosides, carbapenems, cephalosporins, cephazolins, azoles, nitrofurantoins and rifampin. Antimicrobial compositions of the present invention may include one or more antibiotic.

The term "antiseptic" as used herein refers to a compound or agent that is capable of preventing or reducing the growth or reproduction of a microorganism (such as bacteria, fungi, protozoa, and viruses), or of killing a microorganism, but which is generally not applied in the treatment of a systemic infection in a subject, usually because of limitations related to absorption, penetration, or systemic toxicity. A non-limiting class of antiseptics that may be included in an antimicrobial composition of the present invention includes guanidium compounds, such as chlorhexidine. Other examples of antiseptics that may be used include phenoxide antiseptics (e.g., clofoctol, chloroxylenol, triclosan), quaternary ammonium compounds, cetyl pyridinium compounds, iodine compounds, hypochlorites, menthols, eucalyptols, thymols, salicylates, chlorxylenols, aldehydes, glutaraldehyde, peptides, peptide mimetics, acids, bases, oxidizers, gardine, gendine, genlenol, genlosan, or genfoctol.

Chlorhexidine is an antiseptic cleansing agent that is active against staphylococci and other gram-positive bacteria, as well as against various fungi. Chlorhexidine may be included in an antiseptic solution described herein. Chlorhexidine is soluble in both water and organic solutions including alcohols, ketones, ethers, aldehydes, acetonitrile, acetic acid, methylene chloride and chloroform. When utilized herein, the term chlorhexidine may include salts of chlorhexidine. Other antiseptics that may be used instead of or in combination with chlorhexidine include alexidines, octenidines and polyhexamathylbiguanides.

The term "organic solvent" as used herein refers to a solvent that can be used to dissolve antimicrobial agents, and includes, among others, alcohols (e.g., methanol, ethanol), ketones (e.g., acetone, methylethylketone), ethers (e.g., tetrahydrofuran), aldehydes (e.g., formaldehyde), acetonitrile, acetic acid, methylene chloride and chloroform.

The term "penetrating agent" as used herein refers to an agent, such as an organic compound, that is capable of promoting penetration of an antimicrobial agent, such as a guanidium compound, into the matrix of the medical device. Non-limiting examples of such compounds are esters (e.g., ethyl acetate, propyl acetate, butyl acetate, amyl acetate, and combinations thereof), ketones (e.g., acetone and methylethylketone), methylene chloride and chloroform. An antimicrobial solution of the present invention may comprise one or more penetrating agent and/or organic solvent.

The term "alkalinizing agent" as used herein refers to organic and inorganic bases, including sodium hydroxide, potassium hydroxide, ammonia in water (e.g., 27% ammonium hydroxide), diethylamine and triethylamine. An antimicrobial solution of the present invention may comprise an alkalinizing agent.

The term "bacterial and fungal organisms" as used in the present invention means all genuses and species of bacteria and fungi, including but not limited to all spherical, rod-shaped, and spiral bacteria. Non-limiting examples of bacteria include staphylococci (e.g., *Staphylococcus epidermidis, Staphylococcus aureus*), *Enterrococcus faecalis, Pseudomonas aeruginosa, Escherichia coli*, among other gram-positive bacteria and gram-negative bacilli. Non-limiting examples of fungal organisms include *Candida albicans* and *Candida krusei*.

Medical devices that are amenable to treatment according to a method of the present invention generally include non-metallic materials, such as rubber, plastic, polyethylene, polyurethane, silicone, polytetrafluoroethylene (PTFE), polyethylene terephthalate (PET), latex, nitrile, and other polymeric and elastomeric materials, as well as metals, such as titanium, and metal alloys, such as stainless steel and nitinol. Those skilled in the art will appreciate that the listing of non-metals, metals, and metal alloys as described herein is exemplary only, and is not intended to be exclusive. Other materials that are amenable to treatment as described herein are also within the scope of the present invention.

In at least some embodiments set forth herein, the medical device is washed following the sequential contact with the antimicrobial components. As used herein, "washing" refers to the application of a liquid to the medical device for the purpose of removing a substance. For example, washing may be further defined as contacting the surface of the medical device with de-ionized water. The contacting may result in removal of antimicrobial agent and solvent not bound to the medical device. Any method known to those of ordinary skill in the art can be applied in washing the medical device. Washing can, for example, include rinsing, dipping, or immersing the device in a wash solution using any method known to those of ordinary skill in the art.

Additional details regarding contacting an antimicrobial with a medical device not specifically recited herein can be found, e.g., in U.S. Pat. Nos. 5,217,493, 5,624,704, 5,902,283, and 7,651,661, as well as in U.S. Patent App. Pub. Nos. 2005/0197634, 2003/0078242, 2007/0154621, 2008/0183152, 2010/0055086, 2011/0201692, and 2012/0064372 all incorporated by reference.

In some embodiments, an antiseptic solution of the present invention may be heated, e.g., during application to a medical device. As used herein, "heating" refers to an increase in the temperature of a composition due to application of a heat source, when compared to the temperature of the composition in the absence of the heat source. Heating can be by any method known to those of ordinary skill in the art.

II. Glyceryl Nitrates

The present invention is based, in part, on the discovery that glycerol nitrates, such as glyceryl trinitrate (GTN), may be included in an antimicrobial composition in combination with an alcohol and/or a biofilm disrupting agent such as a chelator to kill microbes, e.g., present in a biofilm. As shown in the below examples, it has been observed that GTN can interact synergistically with an alcohol and/or a chelator to kill microorganisms, such as bacteria or fungi.

Glyceryl nitrates include mono-, di-, or trinitrates (e.g., glyceryl mononitrate, glyceryl dinitrate, or glyeryl trinitrate). Mixtures of glyceryl mononitrate, glyceryl dinitrate, and/or glyeryl trinitrate may be used in various embodiments of the present invention. GTN is also referred to as nitroglycerin, nitroglycerine, trinitroglycerin, trinitroglycerine, 1,2,3-trinitroxypropane, and glyceryl trinitrate Various concentrations of a glyceryl nitrate, such as for example GTN, may be used with the present invention. In some embodiments, the glycerol nitrate may be present in an antimicrobial composition or solution of the present invention in an amount of about 0.05-2000, 0.1-2000, 0.1-1750, 0.1-1500, 0.1-1250, 0.1-1000, 1-1000, 10-500, 25-500, 25-250, 50-500, 75-150, or about 10, 20, 30, 40, 50, 60, 70, 80, 90, 100, 110, 120, 130, 140, 150, 160, 170, 180, 190, or 200 micrograms/ml, or any range derivable therein. In some embodiments, intermediate concentrations such as, e.g., 11, 12.5, etc. are contemplated. For example, the concentration of the glyceryl nitrate may be greater than about 10, 11, 12, 13, 14, 15, 20, or 25 micrograms/ml. In some embodiments, the glyceryl nitrate may be in a concentration less than about 2000, 1750, 1500 micrograms/ml. In some embodiments, about 50-125 or about 100 micrograms/ml glyceryl nitrate may be included in a locking solution, such as an intravascular antimicrobial catheter locking solution, as these concentrations can be safely used clinically. In certain preferred embodiments, the glyceryl nitrate is GTN.

A glyceryl nitrate is preferably included in an antimicrobial composition or solution in combination with an additional antimicrobial agent, such as an alcohol or a chelating agent. In some embodiments, about 25-250 micrograms/ml GTN (or other glyceryl nitrate) may be included in an antiseptic composition or solution in combination with, e.g., about 10-70, 15-50, 15-50, 15-30, or about 20%, or any range therein, of an alcohol such as ethanol; these concentrations may be particularly useful in locking solutions or in embodiments where some amount of the antiseptic may be administered or injected into a subject, such as a human patient. In certain preferred embodiments, an antimicrobial composition may comprise greater than 10, 11, 12, 13, 14, 15, 16, 17, 18, 19, or 20% of an alcohol such as ethanol. In some embodiments, an antimicrobial solution may contain about 20% ethanol, about 7% citrate, and about 100 microgram/ml nitroglycerin; these compositions and concentrations may be particularly suitable for safe intravascular antimicrobial catheter lock use.

In some embodiments, a glyceryl nitrate is present in an antimicrobial solution. Although certain preferred embodiments are directed towards solutions, i.e., liquids, comprising a glyceryl nitrate and an additional antimicrobial agent, it is nonetheless anticipated that various gels or semi-solid compositions may be used in various embodiments. In other embodiments the compositions can be allowed to dry such that they form protective antimicrobial coatings that become activated on contact with liquids. In some embodiments, an antimicrobial solution comprising GTN may be a water-based or an aqueous solution. Nonetheless, it is anticipated that non-aqueous solutions of GTN, e.g., comprising an organic solvent or an inorganic nonaqueous solvent (i.e., a solvent other than water) may be used in various aspects of the present invention. The antimicrobial compositions can be applied to ultimately form a coating or be impregnated into articles. In the case of coatings it may be advantageous to include other polymers that bind the glyceryl nitrate compositions on drying.

Although one or more glyceryl nitrate is preferably included in certain preferred embodiments of the present invention, it is anticipated that a nitrate ether or nitroalcohol could be used instead of, or in combination with, a glyceryl nitrate. Non-limiting examples of nitrate ethers which may be included in an antimicrobial composition or solution of the present invention include nitrophenylethers, nitrohalogenatedethers and nitroalkylethers.

III. Alcohols

An antimicrobial solution of the present invention may comprise an alcohol. Non-limiting examples of alcohols that may be used with the present invention include ethanol, methanol, isopropanol, butyl alcohol, propylene glycol, benzyl alcohol, chlorobutanol, phenylethyl alcohol, and the like. In some embodiments, the alcohol may be a polyol such as, e.g., sugar alcohols, diols (e.g., dipropylene glycol), triols (e.g., tripropylene glycols), polyalcohols, etc. In some embodiments, the alcohol may be a glycerol or a glycol such as, e.g., propylene glycol.

The concentration of the alcohol is preferably in the range of 5%-80% (v/v), from about 10% to about 50%, from 15% to 40%, about 20-30%, or about 20%. The alcohol may be present in an antimicrobial solution of the present in at a concentration of, e.g., include 5%, 6%, 7%, 8%, 9%, 10%, 15%, 20%, 25%, 30%, 35%, 40%, 45%, 50%, 55%, 60%, 65%, 70%, 75%, 80% (v/v), or any range derivable therein. In some embodiments, the concentration of the alcohol is greater than about 10, 11, 12, 13, 14, 15, 16, 17, 18, 19, or 20%. In some embodiments, such as preparation of a locking solution, that a lower concentration of the alcohol such as, e.g., from greater than about 10% to about 40%, about 10-30%, or about 20% (v/v) may be used in order to reduce or substantially eliminate toxicity. In addition to the above, the use of intermediate concentrations of alcohol such as 11%, 22.5%, 26% and the like are also contemplated. When alcohol is included in a vascular catheter locking solution, a lower alcohol concentration may have less impact on the physical properties of the plastic the catheter is made from and may reduce risk to the patient whose veins the catheter indwells in. Ethanol can function as a cosolvent with GTN in aqueous solutions, as GTN has low water solubility by itself.

IV. Chelators

An antimicrobial solution comprising GTN may further comprise a biofilm disrupting agent such as a chelator. In some embodiments, the chelator is selected from the group consisting of citrates, a tetra acetic acid, a thiosulfate, N-acetyl cysteine, disulfiram and MesNA. Nonetheless, a wide variety of chelator agents are contemplated as useful in preparing the antimicrobial solutions of the invention. This includes chelators such as EDTA free acid, EDTA 2Na, EDTA 3Na, EDTA 4Na, EDTA 2K, EDTA 2Li, EDTA 2NH.sub.4, EDTA 3K, Ba(II)-EDTA, Ca(II)-EDTA, Co(II)-EDTACu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDS, EDDPO, EDTA-OH, EDTPO, EGTA, HBED, HDTA, HIDA, IDA, Methyl-EDTA, NTA, NTP, NTPO, O-Bistren, THPS, TTHA, EGTA, DMSA, a hydroxy acid, a hydroxamic acid, ethylene diaminedisuccinate (EDDS), Tetrakis hydroxymethyl phosphonium sulfate (THPS), deferoxamine, dimercaprol, zinc citrate, phosphonium chelators, a combination of bismuth and citrate, penicillamine, succimer or Etidronate. It is contemplated that any chelator which binds barium, calcium, cerium, cobalt, copper, iron, magnesium, manganese, nickel, strontium, gallium or zinc will be acceptable for use in the present invention. Other biofilm disrupting agents that can be useful in combination with glyceryl nitrates include enzymes, D-amino acids and quorum sensing inhibitors. In some embodiments, EDDS or THPS may be preferably included in a solution that will be used to clean a pipeline or remove or disinfect a biofilms from an oil pipeline.

In some embodiments the chelator is a hydroxy acid (also called fruit acids) or a hydroxamic acid. The hydroxy acid may comprise, e.g., one or more of lactic acid, gluconic acid, citric acid, galacturonic acid, salicylic acid, glycolic acid, or glucaronic acid. The hydroxamic acid may be hydroxamic acid, benzohydroxamic acid, salicylhydroxamic acid, or suberoylanilide hydroxamic acid (SAHA). Additional hyroxamic acids that may be used with the present invention or included in an antimicrobial solution of the present invention are described in Muri et al. (2002) and Pal and Saha (2012). In some embodiments, the chelator may be present in polymeric form such as polygalacturonic acid, polyglycolic acid, poly lactic acid, polyhydroxamic acids, or copolymers. In some embodiments, the chelator may be present in a latent or protected form such as an ester or anhydride, that can be activated by hydrolysis, e.g., via gluconolactone, or lactide glycolide, etc.

Citrate

"Citrate," as used herein, refers to the conjugate base of citric acid and includes salts of citrate. Citrate in a solution may come from, e.g., trisodium citrate, also called sodium citrate, or any other citrate salt. Various concentrations of citrate may be used with the present invention. For example, about 1, 2, 3, 4, 5, 6, 7, 8, 9, 10, 11, 12, 13, 14, 15, 16, 17, 18, 19, or 20% or more or any range derivable therein may be used. In some embodiments, a concentration of about 1, 2, 3, 4, 5, 6, 7, 8, 9, or 10% or any range derivable therein (e.g., 1-10, 5-9, 5-7.5% etc.) may be included in a locking solution, such as a catheter locking solution. As shown in the below examples, neither 1 mg/ml GTN nor 7% citrate alone were able to eradicate mature biofilms of *Pseudomonas Aeruginosa* or *Candida Albicans* within 2 hours; in combination, 1 mg/ml GTN and 7% citrate was able to fully eradicate these biofilms within this time span.

V. Fatty Acids

In some embodiments, the solution comprises a fatty acid, or a fatty acid ester or anhydride. As shown in the below examples, inclusion of a fatty acid in a composition comprising GTN and a chelator was shown to result in a synergistic killing of microorganisms. These results indicate that the solutions can destroy biofilms very quickly (e.g., within 15-30 minutes or less). In some preferred embodiments, a solution comprising a fatty acid (e.g., a $C_{6-12}$ alkanoic acid or a $C_{6-10}$ alkanoic acid, in combination with a glyceryl nitrate (e.g., GTN) and a chelator may be used as a lock solution in a medical device such as, e.g., a catheter. Generally, the pH of the solution comprising the fatty acid should be below the pK of the fatty acid, such that the fatty acid is protonated. Without wishing to be bound by any theory, it is anticipated that protonation of the fatty acid may be critical or necessary for improved antibacterial activity of the fatty acid. In embodiments where an antimicrobial solution is inserted into a subject, such as a human patient or mammalian non-human animal, the solution may be substantially or completely neutralized to about pH 7, and at this pH the fatty acid may be neutralized and then metabolized as a nutrient by the subject. In embodiments, where the solution is applied to a wound, the wound may display a somewhat reduced pH as compared to the subject, for example a pH of about 5 may be observed in a wound fluid although the mammalian or human subject has blood at about pH 7 throughout the majority of the subject. In some embodiments, although a portion of the fatty acids in the solution may be neutralized when applied to a wound, it is anticipated that a significant and/or synergistic antibacterial killing may occur on the wound as a result of the antimicrobial solution.

The fatty acid may be a $C_{6-12}$ alkanoic acid or more preferably a $C_{6-10}$ alkanoic acid. The fatty acid may be hexanoic acid, decanoic acid, dodecanoic acid, caprylic acid (octanoic acid), caproic acid, or lauric acid. In some embodiments, the fatty acid is caprylic acid.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synergy of Glyceryl Trinitrate with other Components in Antimicrobial Solution

Biofilm eradication experiments were conducted using the Modified Kuhns Biofilm Eradication Model. Briefly, silicone discs made from medical grade elastomer were placed into a 24 well tissue culture plate and incubated overnight in plasma at 37° C. The plasma was then removed and replaced with 1mL of $5.5 \times 10^5$ CFU/mL inoculum of challenge organisms. Methicilin resistant *Staphyloccus aureus* (MRSA), *Pseudomonas aeruginosa* (PA) and *Candida albicans* (CA) were selected as representative virulent gram positive, gram negative and fungal pathogens causing infections. The plates were then incubated for an additional 24 hrs at 37° C. allowing sufficient time for formation of a mature biofilm. Inoculum was then removed and discs were washed shaking for 30 minutes in 0.9% sterile saline. After washing the discs were placed in 1mL of various disinfecting solutions and incubated at 37° C. for 2 hrs. The discs were then removed and placed in 5 mL of 0.9% sterile saline containing neutralizer and sonicated to disrupt any remaining biofilm. The resulting solution was then quantitatively cultured by making serial dilutions in 0.9% sterile saline and plating on agar plates, (TSA+5% sheep blood) for all bacterial organisms and on Sabouraud Dextrose Agar plates for yeasts. Complete eradication of the biofilm requires a recovery of no viable colonies following treatment. Recovery of fewer viable organisms than from the control indicates partial eradication of the biofilm. Results from several experiments showing synergies of Glyceryl Trinitrate (GTN) with chelators and ethanol are tabulated below. Reported results are the viable colonies (in cfu/ml) recovered from the biofilm eradication procedure described above:

| | | | MRSA | PA | CA |
|---|---|---|---|---|---|
| Experiment 1: Control and Components Individually | | | | | |
| control | | | 5.00E+05 | 5.00E+05 | 5.00E+05 |
| Citrate (7%) | | | 2.92E+04 | 2.24E+04 | 2.16E+04 |
| GTN (1 mg/ml) | | | 5.00E+03 | 2.05E+03 | 5.00E+03 |
| MesNA (5%) | | | 5.00E+05 | 5.00E+05 | 5.00E+05 |
| Disulfiram (0.2 mg/ml) | | | 2.00E+04 | 5.00E+05 | 0.00E+00 |
| Experiment 2: Synergy of Citrate and GTN against PA and CA | | | | | |
| GTN (0.5 mg/ml) | citrate (7%) | | 5.00E+03 | 0.00E+00 | 4.40E+03 |
| GTN (1 mg/ml) | citrate (7%) | | 5.00E+03 | 0.00E+00 | 0.00E+00 |
| Experiment 3: Synergy of GTN and MesNA against PA | | | | | |
| GTN (1 mg/ml) | MesNA (5%) | | 5.00E+03 | 0.00E+00 | 5.85E+03 |
| Experiment 4: Synergy of GTN + citrate + Disulfiram | | | | | |
| GTN (0.2 mg/ml) | citrate (7%) | Disulfiram (0.2 mg/ml) | 2.50E+02 | 0.00E+00 | 0.00E+00 |
| Experiment 5: Synergy of GTN + MesNA + Citrate | | | | | |
| GTN (0.1 mg/ml) | Mesna (5%) | citrate (7%) | 5.00E+03 | 0.00E+00 | 3.00E+04 |
| Experiment 6: Ethanol + citrate (baselines) | | | | | |
| citrate (7%) | ethanol (10%) | | 5.00E+03 | 0.00E+00 | 5.50E+02 |
| citrate (7%) | ethanol (15%) | | 5.00E+03 | 0.00E+00 | 0.00E+00 |
| citrate (7%) | ethanol (20%) | | 2.10E+03 | 0.00E+00 | 0.00E+00 |
| Experiment 7: Synergies of GTN + Ethanol + citrate | | | | | |
| citrate (7%) | ethanol (10%) | GTN (0.5 mg/ml) | 0.00E+00 | 0.00E+00 | 0.00E+00 |
| citrate (7%) | ethanol (10%) | GTN (0.2 mg/ml) | 3.50E+03 | 0.00E+00 | 0.00E+00 |
| citrate (7%) | ethanol (15%) | GTN (0.2 mg/ml) | 0.00E+00 | 0.00E+00 | 0.00E+00 |
| citrate (7%) | ethanol (15%) | GTN (0.1 mg/ml) | 5.00E+03 | 0.00E+00 | 0.00E+00 |
| citrate (7%) | ethanol (20%) | GTN (0.1 mg/ml) | 0.00E+00 | 0.00E+00 | 0.00E+00 |
| citrate (7%) | ethanol (20%) | GTN (0.05 mg/ml) | 5.00E+03 | 0.00E+00 | 0.00E+00 |

These results show that the concentration of GTN can be reduced 10-fold (to 100 microgram/ml) to what otherwise would be needed by itself, in the presence of ethanol and citrate, to fully eradicate mature biofilms within 2 hours. These levels attain those which are safe concentrations for intravenous or topical use. Similar synergy is seen with GTN and single or combinations of other chelators (GTN and citrate against CA and PA, GTN and MesNA against PA, GTN, citrate and Disulfiram against MRSA and PA, and GTN, citrate and MesNA against PA). The ethanol-citrate-GTN composition is particularly useful for vascular catheter antimicrobial lock therapy where it can more safely and economically eliminate the need for antibiotics or high ethanol concentrations required for colonized catheter salvage.

The synergies are graphically illustrated in FIGS. 1-7. FIGS. 1A-B illustrates synergy of GTN and citrate for GTN at 0.5 mg/ml concentration against *P. aeruginosa* and additionally for GTN at 1 mg/ml concentration against *C. albicans*.

Figure 5:
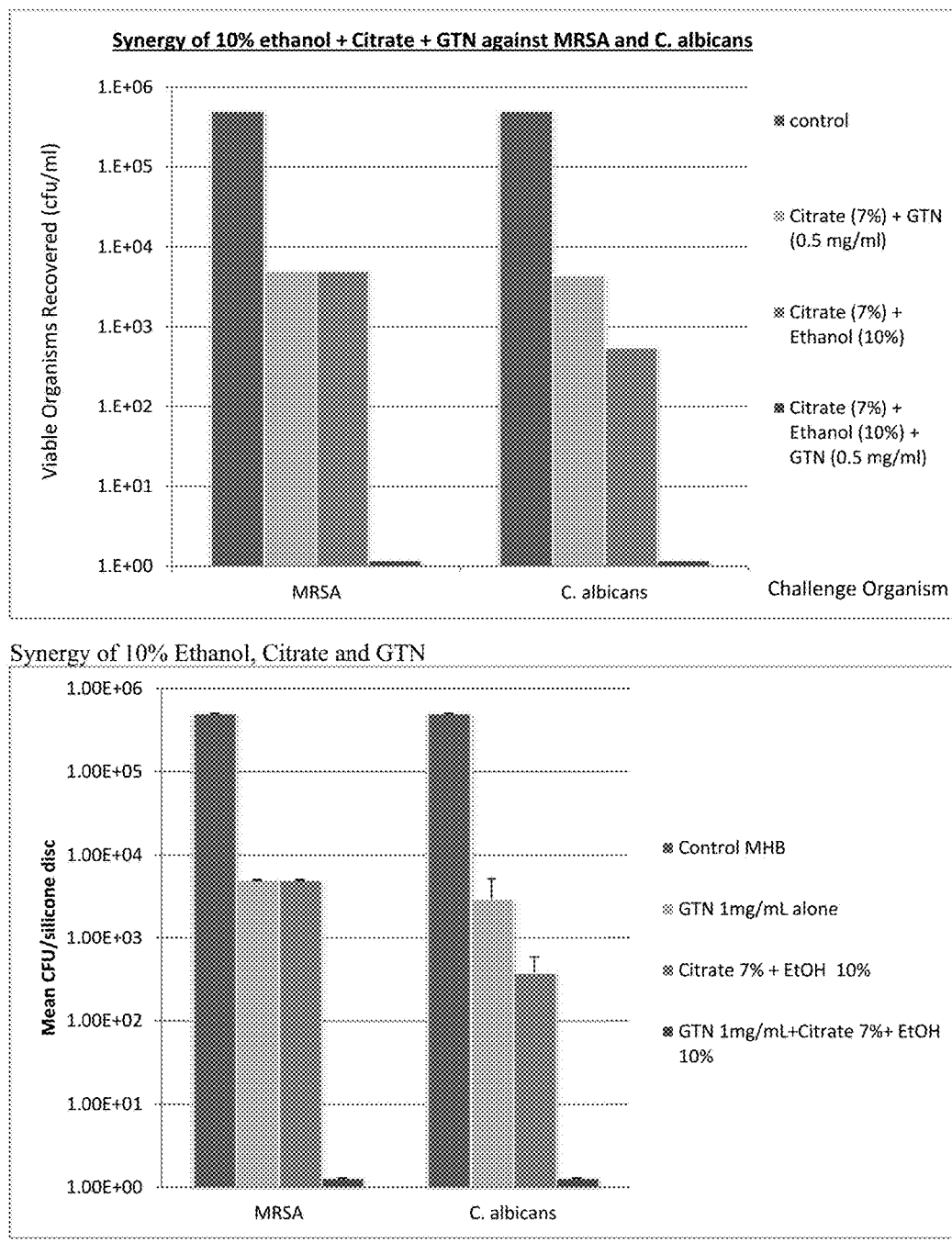
FIG. 5: Synergy of 10% Ethanol, Citrate and GTN.
Figure 6:
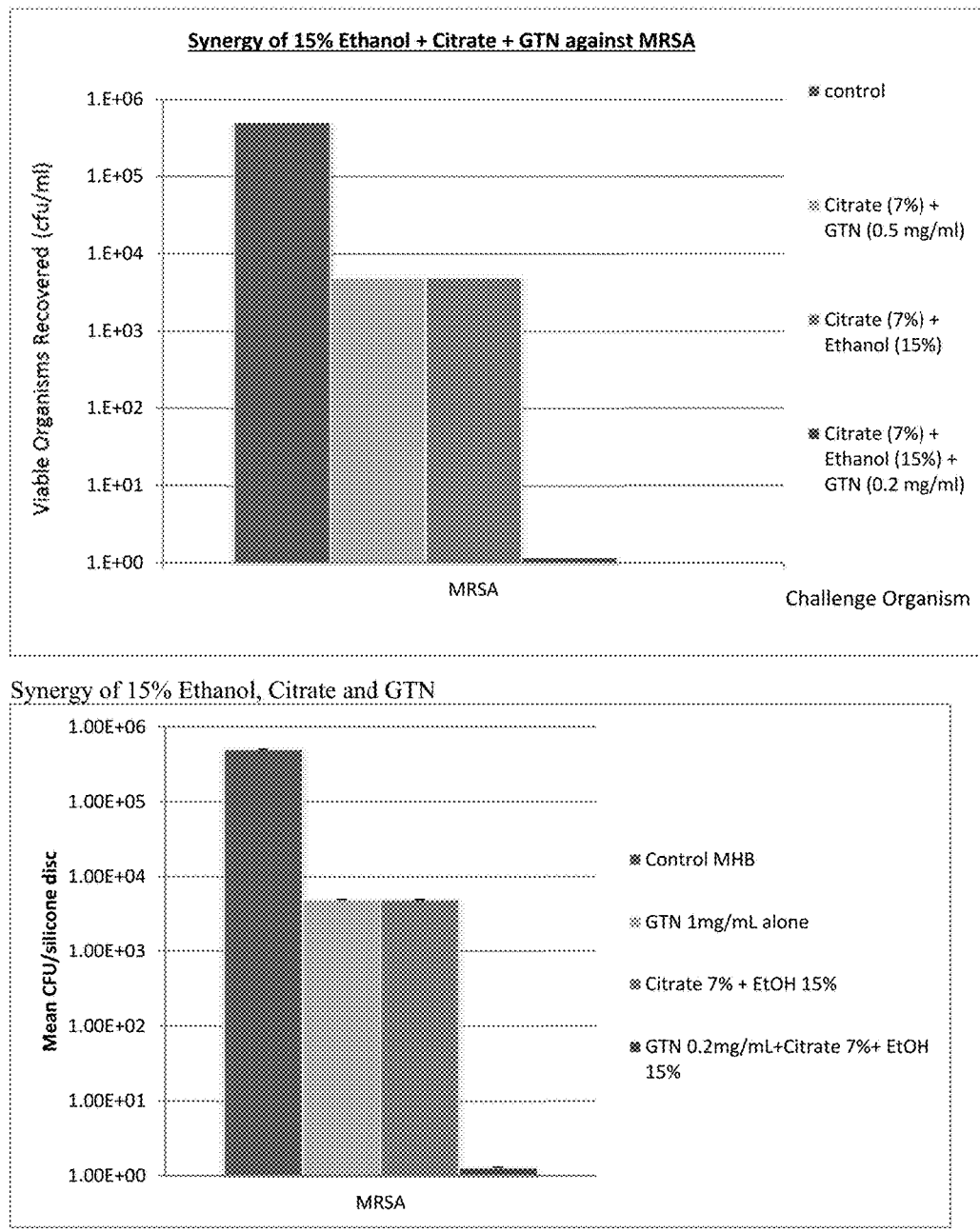
FIG. 6: Synergy of 15% Ethanol, Citrate and GTN.
Figure 8:
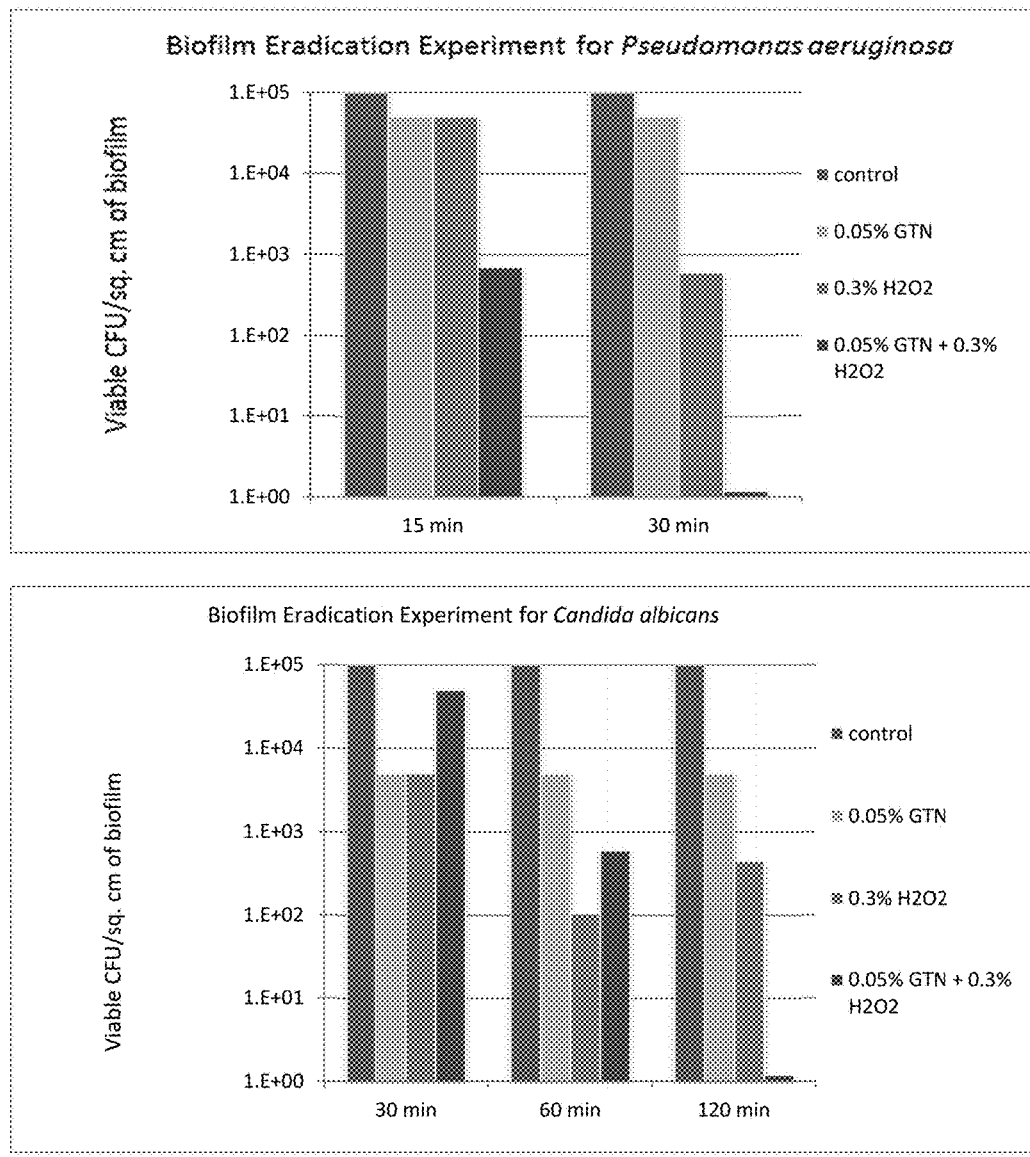
FIG. 8: Synergies of 0.05% GTN and 0.3% Hydrogen Peroxide ($H_2O_2$—a bioenhancer)
Figure 9:
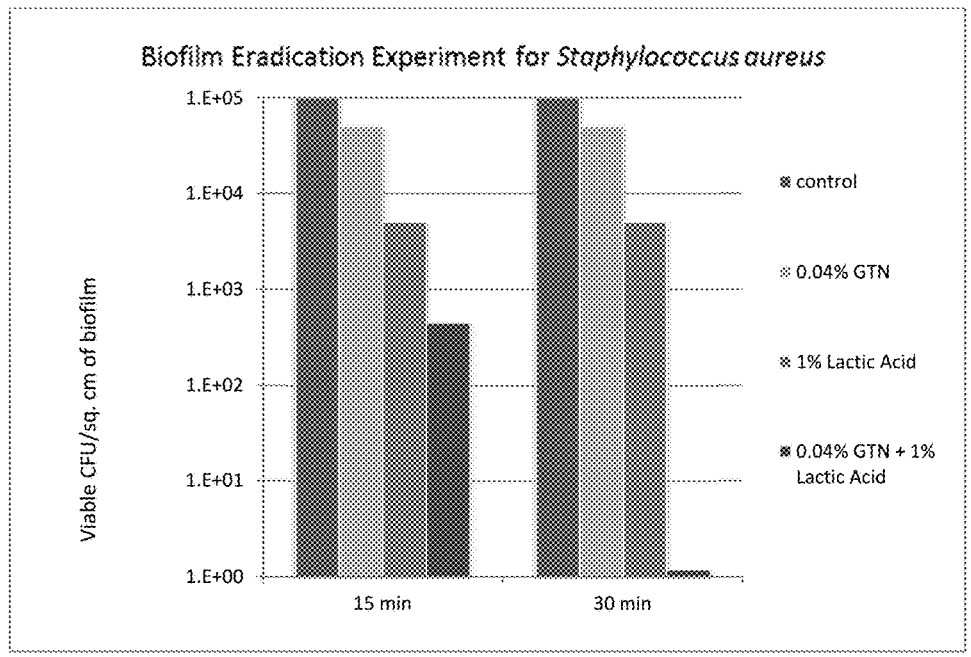
FIG. 9: Synergy of GTN and Lactic Acid (an acidic chelator)
Figure 10:
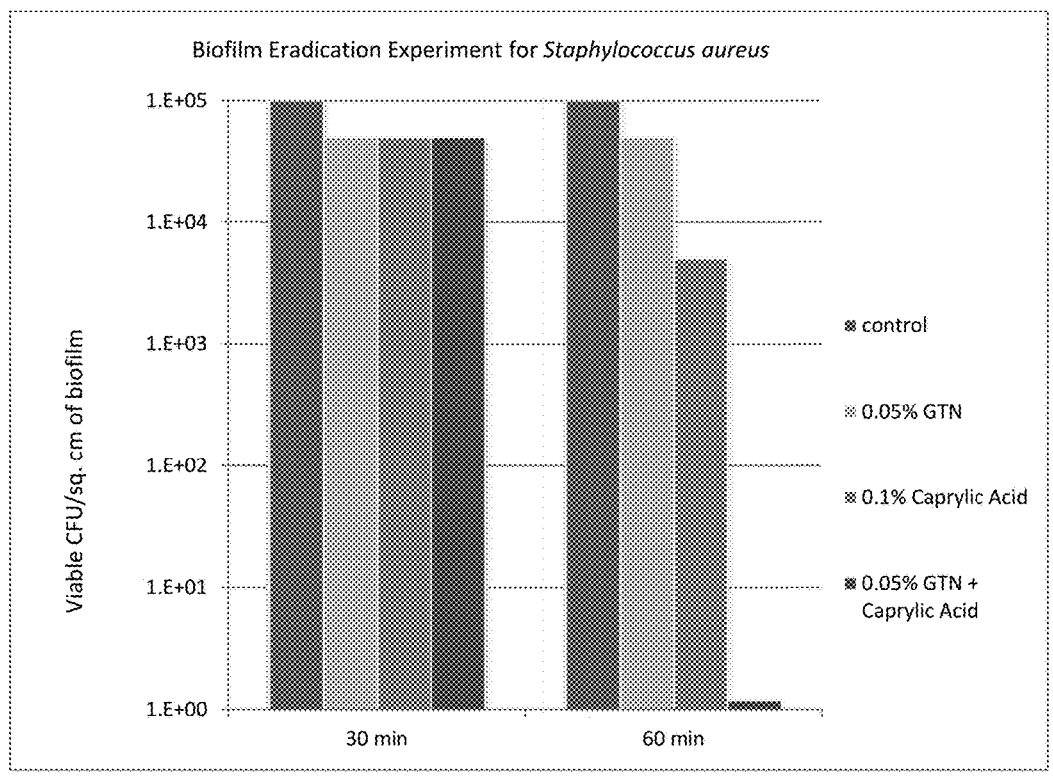
FIG. 10: Synergy of GTN and Caprylic Acid (a bioenhancer). Solution was adjusted to pH 4.7.
Figure 11:
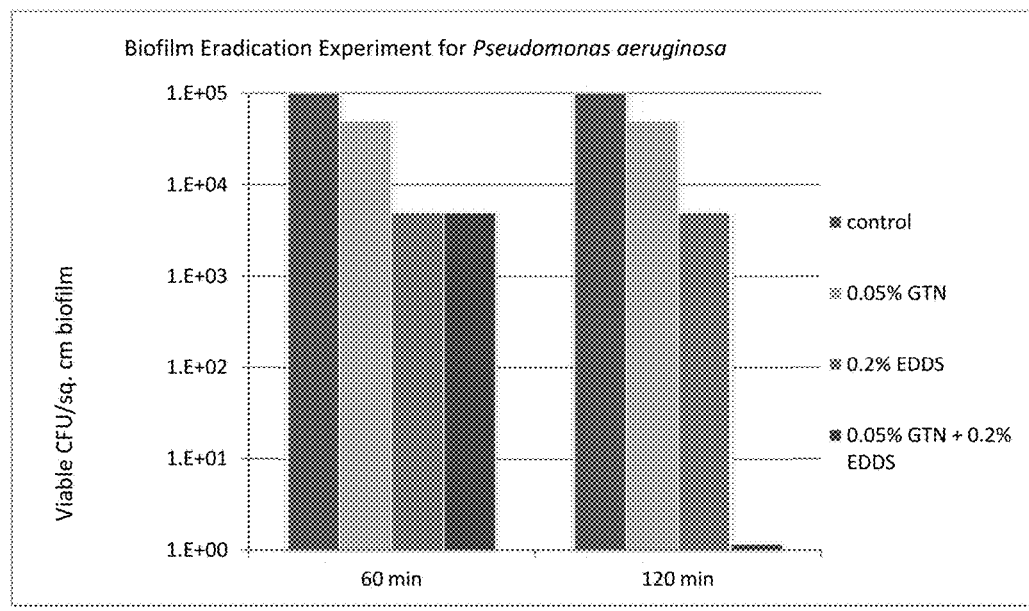
FIG. 11: Synergy of GTN and ethylene diaminedisuccinate (EDDS—a chelator)
Figure 12:
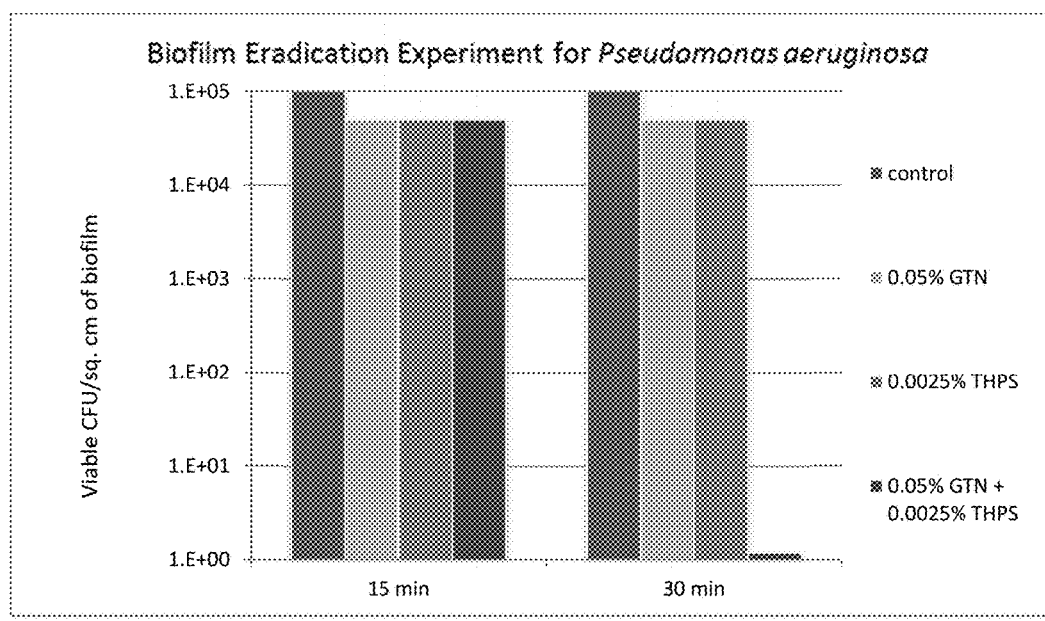
FIG. 12: Synergy of GTN and tetrakis hydroxymethyl phosphonium sulfate (THPS—a biocidal chelator)
Figure 13:
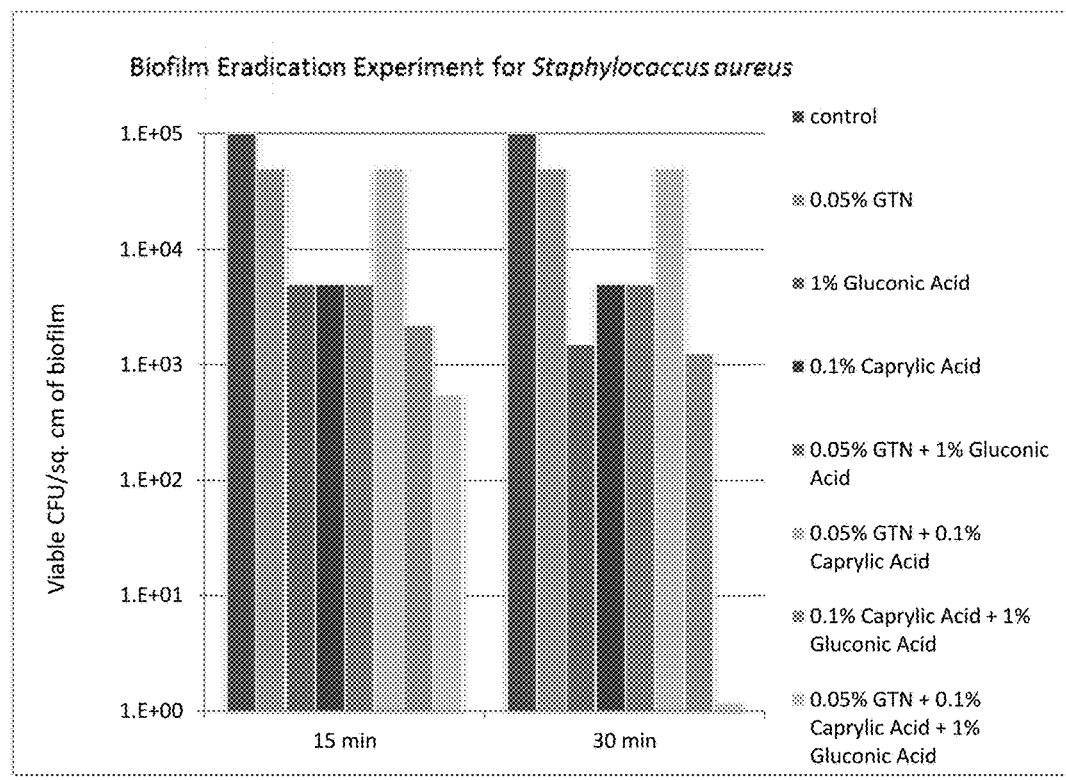
FIG. 13: Synergy of GTN+Caprylic Acid and Gluconic Acid (an acidic chelator). The pH was not adjusted.
Figure 14:
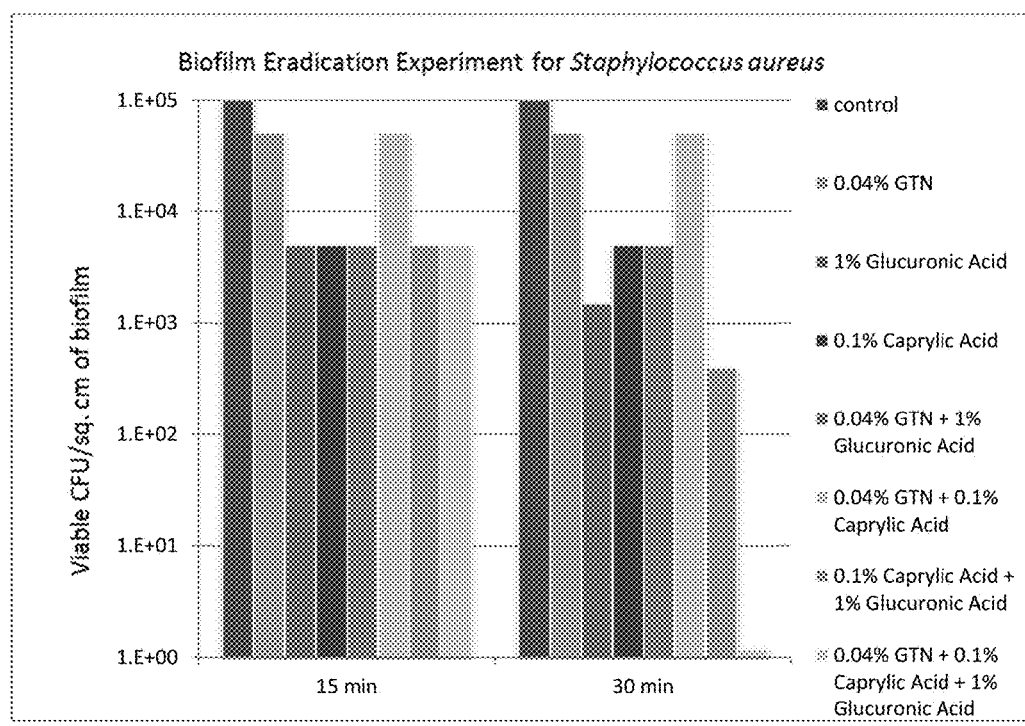
FIG. 14: Synergy of GTN+Caprylic acid+Glucuronic acid (an acidic chelator). The pH was not adjusted.

FIGS. 5-7 show GTN synergies with citrate at a series of ethanol concentrations. Specifically the series of Figures show how the synergistic GTN concentration can be reduced as ethanol concentration is increased. FIG. 5 shows that at 10% ethanol and 7% citrate, a GTN concentration of 0.2 mg/ml eradicated *P.aeruginosa* and *C. albicans* and a GTN concentration of 0.5 mg/ml fully eradicated MRSA. FIG. 6 shows that when the ethanol concentration is increased to 15%, the GTN concentration required to eradicate to eradicate MRSA was reduced to 0.2 mg/ml. FIG. 7 shows that when the ethanol concentration is further increased to 20%, the GTN concentration required to eradicate MRSA is reduced to 0.1 mg/ml.

Example 2

Compositions for Inhibiting Biofilms Utilizing Glyceryl Nitrates

Additional biohancers, chelators and combinations were studied in combination with GTN against *Staphylococcus aureus*, *Pseudomonas aeruginosa* and *Candida albicans* biofilms. Biofilm eradication studies (similar to experiments 1-7) were run on silicone disks where biofilms were allowed to form for 24 hours. Exposure times to disinfecting solutions was for times ranging from 15 minutes to 2 hours followed by quantitative enumeration of viable colony forming units (CFU) per square cm of disk by sonication and quantitative plating. Examples of synergy of hydrogen peroxide, lactic acid, caprylic acid, ethylene diaminedisuccinate, tetrakishydroxymethyl phosphonium sulfate, gluconic acid, and glucuronic acid with GTN are shown in FIGS. 8-14. These solutions may be used, e.g., to disinfect a catheter as a lock solution.

Figure 15:
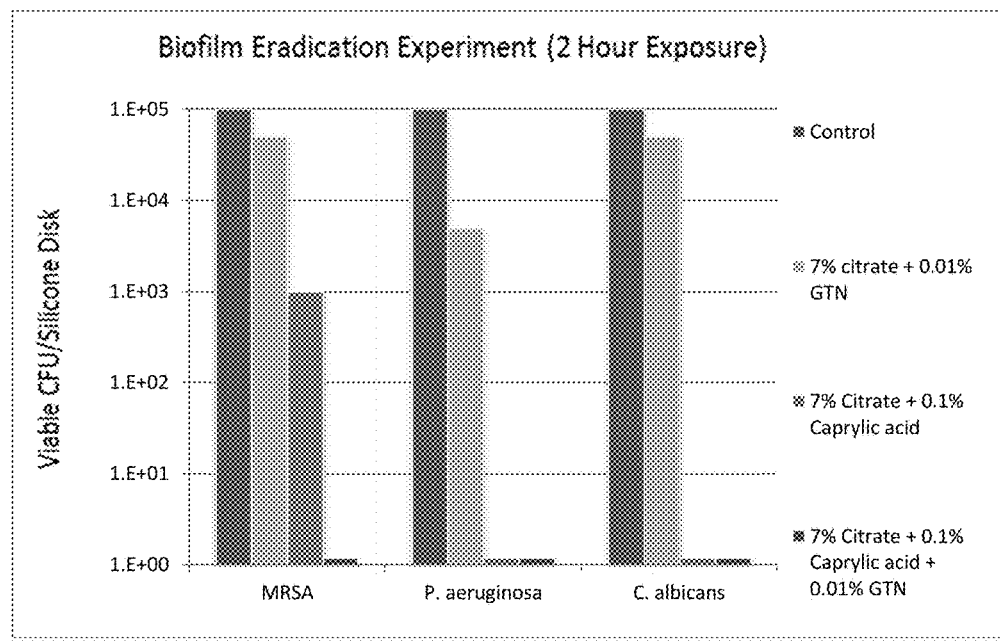
FIG. 15: Substitution of Caprylic Acid for Ethanol in 7% Citrate+0.01% GTN+20% Ethanol Antimicrobial Solution.
Figure 16:
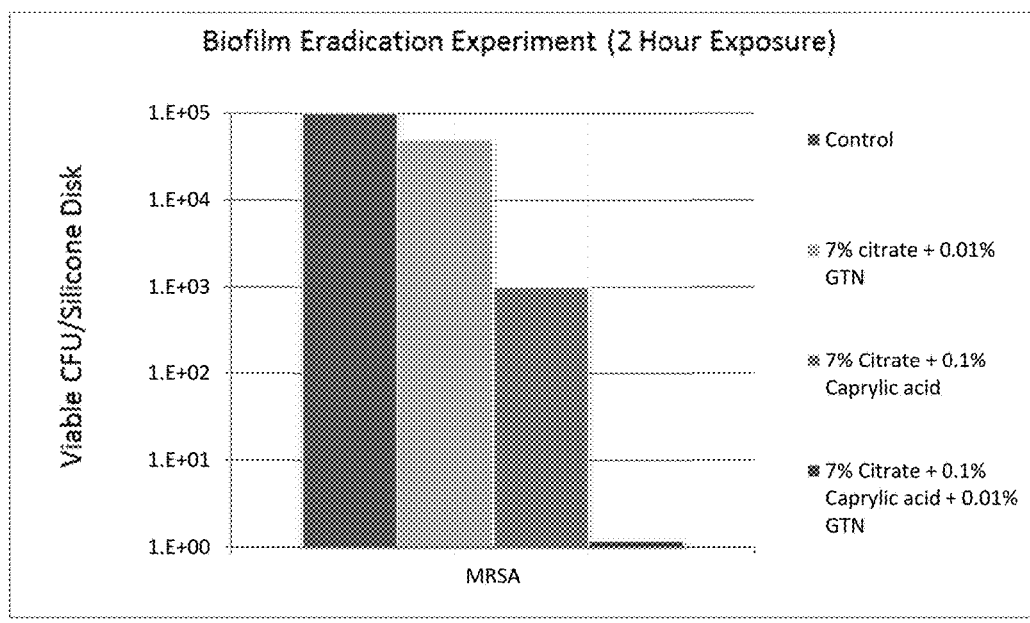
FIG. 16: Synergy of 7% Citrate+0.1% Caprylic Acid+0.01% GTN.

The experiment tested whether the 7% Citrate+0.01% GTN+20% Ethanol composition could eradicate all 3 model organisms by substituting 0.1% Caprylic acid for the 20% Ethanol. The caprylic acid solution was acidified to pH 4.7. Results for a 2 hour biofilm eradication experiment are presented in FIG. 15. Complete eradication of biofilms of all organisms within 2 hours is seen with 7% citrate+0.01% GTN and 0.1% Caprylic acid at pH 4.7 as was seen with 7% Citrate+0.01% GTN+20% Ethanol. Similar synergy to FIG. 7 (0.01% GTN+7% Citrate+20% Ethanol) is seen for MRSA with in FIG. 16 (0.01% GTN+7% Citrate+0.1% Caprylic acid). Note that 0.1 mg/ml is the same as 0.01% in comparing FIGS. 7 and 16.

Figure 17:
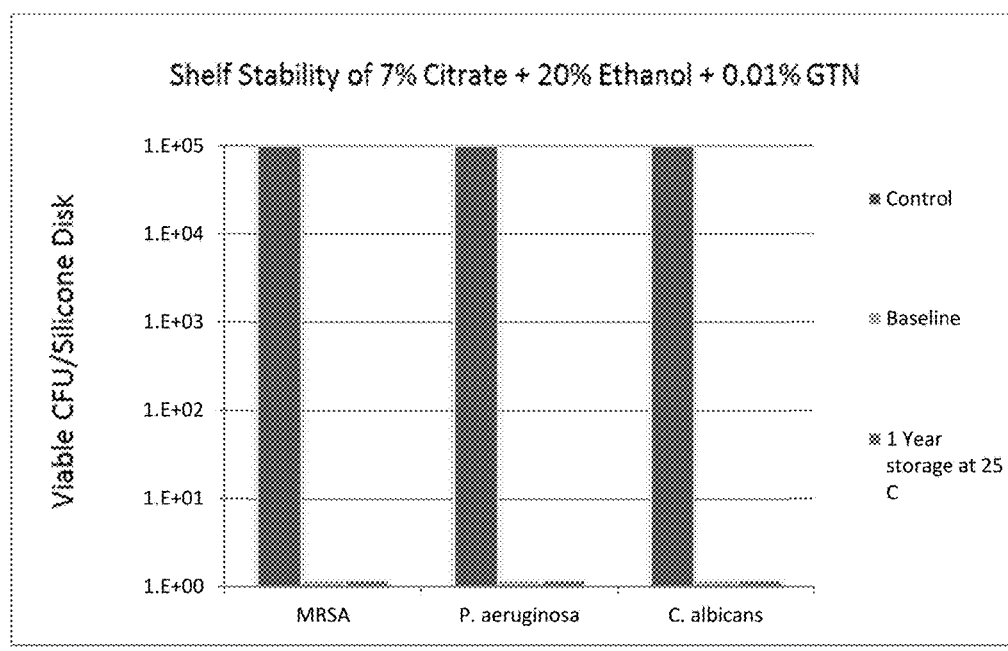
FIG. 17: 1 year Shelf Stability of 7% Citrate+20% Ethanol+0.01% GTN.

Shelf stability of the 7% Citrate+0.01% GTN+20% Ethanol solution was tested following 1 year of storage at 25° C. The solution was stored in a glass container and was protected from light exposure. Comparison of baseline biofilm eradication effectiveness (FIG. 7) and effectiveness following 1 year storage is shown in FIG. 17. The antimicrobial activity of the 7% Citrate+20% Ethanol+0.01% GTN solution was unchanged following 1 year storage at 25° C. These examples clearly show a synergy between GTN and hydrogen peroxide, lactic acid, caprylic acid, ethylene diaminedisuccinate, tetrakishydroxymethyl phosphonium sulfate, gluconic acid, and/or glucuronic acid.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 5,217,493, 5,624,704, 5,902,283, and 7,651,661;

U.S. Patent App. Pub. Nos. 2005/0197634, 2003/0078242, 2007/0154621, 2008/0183152, 2010/0055086, 2011/0201692, and 2012/0064372;

Slobbe et al, Prevention of Catheter-Related Bacteremia with a Daily Ethanol Lock in Patients with Tunnelled Catheters: A Randomized, Placebo-Controlled Trial, PLoS ONE 5(5): e10840

Crnich et al., Prospective Randomized Double-Blind Trial of an Ethanol Lock for Prevention of CLABSI [Abstract]. In: 49th Interscience Conference on Antimicrobial Agents and Chemotherapy. San Francisco, USA. 2009

Muri et al. Hydroxamic acids as pharmacological agents. *Curr Med Chem.* September; 9(17):1631-53, 2002.

Pal and Saha Hydroxamic acid—A novel molecule for anticancer therapy. *J Adv Pharm Technol Res.* April-June; 3(2): 92-99, 2012.

The invention claimed is:

1. An antimicrobial solution comprising a glyceryl nitrate and ethanol at a level from about 10%-50% (v/v), and a chelator, wherein the chelator is citrate at an amount of 0.1-10% (v/v); and wherein the solution is a pharmaceutically acceptable composition.

2. The solution of claim 1, wherein the glyceryl nitrate is glyceryl trinitrate (GTN).

3. The solution of claim 2, wherein the glyceryl trinitrate has a concentration of from about 0.05 to about 1500 micrograms/ml.

4. The solution of claim 3, wherein the glyceryl trinitrate has a concentration of from about 1 to about 1000 micrograms/ml.

5. The solution of claim 4, wherein the glyceryl trinitrate has a concentration of from about 10 to about 500 micrograms/ml.

6. The solution of claim 1, wherein the citrate comprises about 1-10% (v/v) of the solution.

7. The solution of claim 6, wherein the citrate comprises about 3.5-7% of the solution.

8. The solution of claim 7, wherein the citrate comprises about 4% of the solution.

9. The solution of claim 1, wherein the concentration of the ethanol is in the range of from greater than 10 to about 40%.

10. The solution of claim 9, wherein the concentration of ethanol is in the range of from about 15-30% (v/v).

11. The solution of claim 1, wherein the concentration of the ethanol is about 20%-30%.

12. The solution of claim 1, wherein the solution comprises from greater than 10% to about 30% ethanol, about 1-20% citrate, and about 10-500 microgram/ml glyceryl trinitrate.

13. The solution of claim 1, wherein the solution comprises from about 15% to about 30% ethanol, about 2.5-10% citrate, and about 50-250 microgram/ml glyceryl trinitrate.

14. A method for reducing microbial organisms from a surface comprising contacting the surface with an antimicrobial solution of claim 1 for an amount of time sufficient to reduce microbial organisms on the surface.

15. The method of claim 14, wherein the microbial organisms are present in a biofilm on the surface.

16. The method of claim 14, wherein the surface is comprised on a catheter.

17. The method of claim 16, wherein the surface is comprised on the interior of a vascular catheter.

18. A kit comprising the solution of claim 1 in a suitable container means.

19. The kit of claim 18, further comprising instructions for use.

20. The kit of claim 18, wherein the suitable container means is a vial, syringe or dispenser.

21. The kit of claim 18, wherein the solution is comprised in or on a swab or wipe.

22. A method of treating a wound in a subject comprising administering or contacting the solution of claim 1 to at least a portion of the wound.

23. The method of claim 22, wherein the subject is a human.

24. The method of claim 22, wherein the solution is topically administered to the subject.

25. The method of claim 22, wherein the solution is administered as a lavage.

26. The method of claim 22, further comprising irrigating the wound with the solution.

27. The method of claim 22, wherein the solution is applied to a wound bed, an epithelial tissue, an endothelial tissue, or an organ surface.

28. The method of claim 22, wherein the solution is used a locking solution in a catheter.

29. The method of claim 11, wherein the concentration of the ethanol is about 20%-25%.

30. The method of claim 20, wherein the suitable container means is a syringe.

31. The kit of claim 18, wherein the solution in is comprised in a cream or ointment.

32. The solution of claim 1, wherein the solution is further defined as a catheter locking solution.

33. The solution of claim 1, wherein the glyceryl nitrate is glyceryl trinitrate, and wherein the solution comprises about 15%-25% ethanol, about 2.5-10% citrate, and about 1-100 micrograms/ml glyceryl trinitrate.

34. The solution of claim 33, wherein the solution comprises about 2.5-7% citrate.

35. The solution of claim 34, wherein the solution comprises about 10-50 micrograms/ml glyceryl trinitrate.

36. The solution of claim 34, wherein the solution comprises about 20-40 micrograms/ml glyceryl trinitrate.

37. The solution of claim 36, wherein the solution comprises about 30 micrograms/ml glyceryl trinitrate.

38. The solution of claim 36, wherein the solution comprises about 20-25% ethanol.

39. The solution of claim 38, wherein the solution comprises about 20-22.5% ethanol.

40. The solution of claim 36, wherein the solution comprises about 3-6% citrate.

41. The solution of claim 40, wherein the solution comprises about 3-5% citrate.

42. The solution of claim 41, wherein the solution comprises about 4% citrate.

43. The solution of claim 33, wherein the solution comprises about 20-22.5% ethanol, about 4% citrate, and about 30 micrograms/ml glyceryl trinitrate.

* * * * *